(12) United States Patent
Steinbrenner

(10) Patent No.: US 7,939,320 B2
(45) Date of Patent: May 10, 2011

(54) ASTAXANTHINE BIOSYNTHESIS IN EUKARYOTES

(75) Inventor: Jens Steinbrenner, Constance (DE)

(73) Assignee: Peter und Traudl Engelhorn-Stiftung zur Forderung der Biotechnologie und Centechnik, Stuttgart (DE)

( * ) Notice: Subject to any disclaimer, the term of this patent is extended or adjusted under 35 U.S.C. 154(b) by 419 days.

(21) Appl. No.: 12/083,395

(22) PCT Filed: Oct. 12, 2006

(86) PCT No.: PCT/EP2006/009881
§ 371 (c)(1),
(2), (4) Date: Apr. 9, 2008

(87) PCT Pub. No.: WO2007/042304
PCT Pub. Date: Apr. 19, 2007

(65) Prior Publication Data
US 2010/0129845 A1   May 27, 2010

(30) Foreign Application Priority Data

Oct. 13, 2005 (DE) .......... 10 2005 049 072

(51) Int. Cl.
*C12N 15/00* (2006.01)
*C12N 5/00* (2006.01)
*C12N 5/04* (2006.01)
*C12N 1/20* (2006.01)
*C12N 9/02* (2006.01)

(52) U.S. Cl. ............ 435/320.1; 435/410; 435/413; 435/418; 435/189; 536/23.2

(58) Field of Classification Search .......... 435/29, 435/67, 189, 320.1, 417, 468; 536/23.2
See application file for complete search history.

(56) References Cited

U.S. PATENT DOCUMENTS 6,677,134 B2 * 1/2004 Pasamontes et al. .......... 435/67
* cited by examiner

*Primary Examiner* — Tekchand Saidha
(74) *Attorney, Agent, or Firm* — Fulbright & Jaworski L.L.P.

(57) ABSTRACT

The invention relates to a DNA vector comprising (a) a DNA sequence coding for the phytoene desaturase protein that is modified in one position by an amino add exchange providing resistance, and (b) a multiple cloning site into which any DNA sequence can be cloned. The invention also relates to the use of said DNA vector for transforming enkaryotic cells, transformation methods, and transgenic plant cells produced in said manner.

18 Claims, 9 Drawing Sheets

Figure 1:
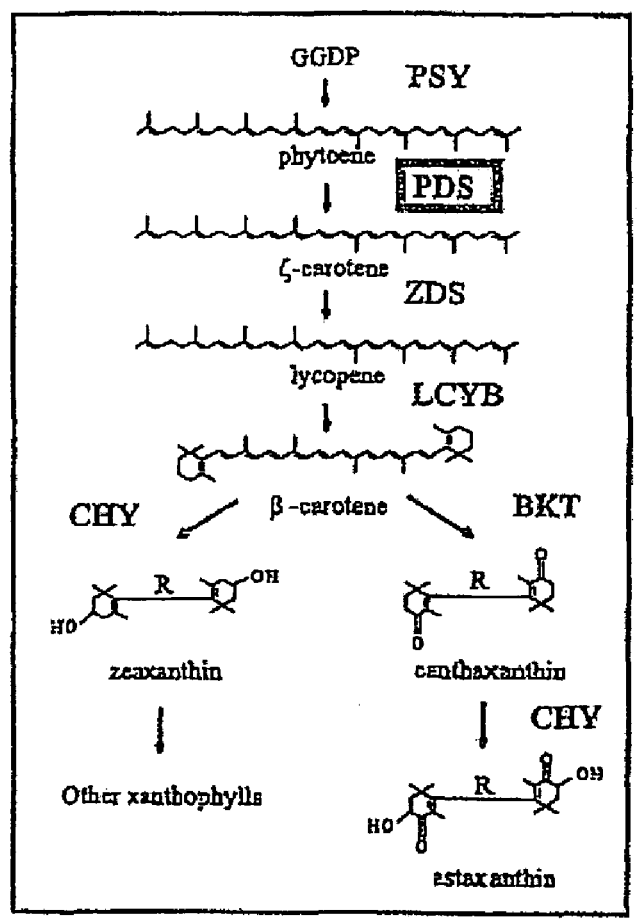

RF: Resistance factor for the herbicide norflurazon
TP: Transit peptide for the import into chloroplasts

Figure 3

```
CLUSTAL W (1.82) multiple sequence alignment

PDS_H.pluvialis       HQTTHRGQASGSGCTSGRQARGHVSRRSVRERGALRVVAKDYPTPDFQSS  50       SEQ ID NO. 2
PDS_Synechococcus7942 --------------------------------------------------          SEQ ID NO. 10

PDS_H.pluvialis       DTYQEALSLSTKLRNAPRPAKPLRVVIAGAGLAGLSAAKYLADAGHHPVV 100
PDS_Synechococcus7942 ----------------------MRVAIAGAGLAGLSCAKYLADAGHTPIV  28
                                            :** *********.******** **:*

PDS_H.pluvialis       LEGRDVLGGKVAAWKDEDGDHYETGLHIFFGAYPNIQNLFKELGIQDRLQ 150
PDS_Synechococcus7942 YERRDVLGGKVAAWKDEDGDHYETGLHIFFGAYPNMLQLFKELNIEDRLQ  78
                       *.*****************************: :**:****. *:***

PDS_H.pluvialis       WKEHSNIFAKPDAPGEFSRFDFPELPAPWNGIIAILRNNQHLSWPEKIRF 200
PDS_Synechococcus7942 WRSHSHIFNQPTKPGTYSRFDFPDIPAPINGVAAILSNNDMLTWEEKIKF 128
                      *:.**:** :*..**.:******::*** **:.*** **::*:*.**:*

PDS_H.pluvialis       RIGLLPAIIFGQRYCEEQDELTVTEWHRKQGVPDRVNEEVFIAMAKALNF 250
PDS_Synechococcus7942 GLGLLPAWIRGQSYVEEMDQYSWTEWLRKQNIPERVNDEVFIAMAKALNF 178
                       :*****.* **.* **:*: :.**: ***::*:***:***********

PDS_H.pluvialis       INPDDLSHTVVLTALNRFLQEQHGSKMAFLDGAPPERLCQPHVDYFKARG 300
PDS_Synechococcus7942 IDPDEISATVVLTALNRFLQEKKGSMMAFLDGAPPERLCQPIVEHVQARG 228
                      *:**::*.*****.*******::**:**************:*:::.:**

PDS_H.pluvialis       GDLHFNSRVKQIVLNDDKSVKHLALT------NGQTVEGDLYISAMPVDM 345
PDS_Synechococcus7942 GDVLLNAPLKEFVLNDDSSVQAFRIAGIKGQEEQLIEADAVVSALPVDPL 278
                      **::: : :*::*****.**: : :        *  :*.*  :*:***

PDS_H.pluvialis       KILMPDPWASHPYFKQLNGLEGVPVINIHIWFDRKLTTVDHILFSRSPLL 395
PDS_Synechococcus7942 KLLLPDAWKAMPYFQQLDGLQGVPVINIHLWFDRKLTDIDHILFSRSPLL 328
                      *:::**.* :.***:**:**:********:******* :*****.****

PDS_H.pluvialis       SVYADMSTTSKEYRDDKKSHLELVFAPAKEWIGRPDEEIIAATHTELERL 445
PDS_Synechococcus7942 SVYADMSNTCREYEDPDRSHLELVFAPAKDWIGRSDEDILAATMAEIERL 378
                      *******.*..:**.  :*********:****.**:*:***   ::***

PDS_H.pluvialis       FPTEVRADQSHAKILRYKVVKTPLSVYKTAGREKFRPTQRSPISNFYLA 495
PDS_Synechococcus7942 FPQHFSGEN-PARLRKYKIVKTPLSVYKATPGRQQYRPDQLSPIANFFLT 427
                      **  . .:: *:::* ** ********:: **::.**.* ***:**:*:

PDS_H.pluvialis       GDYTKQKYLASMEGAVFSGKLVTEAIVEDHSARGVTSSAASRQPALAAAG 545
PDS_Synechococcus7942 GDYTHQRYLASMEGAVLSGKLTAQAIIARQDELQRRSSGRP----LAASQ 473
                      ****:::::.******:****.::**:   .   ..**.**    *:*.

PDS_H.pluvialis       VVGRVGSSDWARWLQPVGAIAGGCK 570
PDS_Synechococcus7942 A------------------------ 474
```

ASTAXANTHINE BIOSYNTHESIS IN EUKARYOTES

RELATED APPLICATIONS

This application is a §371 of PCT/EP2006/009881 filed Oct. 12, 2006, which claims priority from German Patent Application No: 10 2005 049 072.7 filed Oct. 13, 2005.

The invention relates to a DNA vector which comprises (a) a DNA sequence which codes for the protein phytoene desaturase which is modified at one position by a resistance-conferring amino acid substitution and (b) a multiple cloning site into which any DNA sequence can be cloned, to its use for the transformation of eukaryotic cells, to transformation methods, and to transgenic plant cells thus prepared.

BACKGROUND OF THE INVENTION

Carotenoids are pigments which are found in all photosynthetic organisms. They play an important role as components of the photosynthetic reaction center and in mediating protection against photooxidative damage.

The carotenoid biosynthetic pathway proceeds from geranylgeranyl diphosphate (GGDP) to astaxanthin. As the result of the condensation of two molecules of geranylgeranyl pyrophosphate, the phytoene synthase enzyme (PSY) forms the C40 structure phytoene. Starting from phytoene, the phytoene desaturase enzyme (PDS) synthetizes ζ-carotene by eliminating protons and incorporating two double bonds. The intermediate of this synthetic step is phytofluene. ζ-Carotene, in turn, is converted into lycopene in a two-step desaturation reaction, which proceeds via the intermediate neurosporin. The enzyme which is responsible therefor is ζ-carotene desaturase (ZDS). Lycopene is converted into β-carotene via a lycopene cyclase (LCYB). Starting from β-carotene, two further enzymes are involved in the formation of astaxanthin. Firstly, the β-carotene ketolase enzyme (BKT) introduces in each case one keto group at the 4 and the 4' position. Secondly, in each case one hydroxyl group is attached at the 3 and 3' positions on the ion ring of the astaxanthin precursor via the carotenoid hydroxylase enzyme (CHY).

Overexpressing a bacterial phytoene synthase from *Eriwinia uredovora* has made it possible to influence, or stimulate, carotenoid biosynthesis in transgenic tomato plants and thus to increase the amount of carotenoid synthesized by a factor of 2-4 (Fraser, Romer et al. 2002).

However, it is the enzyme phytoene desaturase which plays the central key role in the carotenoid biosynthetic pathway (FIG. 1). The pds genes, which code for phytoene desaturase, have been cloned from cyanobacteria (Chamovitz et al., 1991; Martínez-Férez and Vioque, 1992; Martínez-Férez et al., 1994) and higher plants (Bartley et al., 1991; Pecker et al., 1992) and are successfully overexpressed in *E. coli*. The bleaching herbicide norflurazon is known as a reversible, noncompetitive inhibitor of phytoene desaturase. Mutated forms of phytoene desaturase have been described for the cyanobacterium *Synechococcus*; they confer resistance to norflurazon to the bacterium. In each case, the resistance-imparting mutations are based on a single amino acid substitution. Within the scope of the mutation studies carried out in *Synechococcus*, resistances have been found for the following amino acid substitutions: Arg195Pro; Leu320Pro; Val403Gly; Leu437Arg (Linden et al., 1990; Chamovitz et al., 1993). Despite the fact that norflurazon and other such bleaching herbicides have been used for some time for controlling weeds, no resistant naturally occurring plants have been isolated to date.

Among the intermediates and products of the carotenoid biosynthetic pathway, it is in particular the keto carotenoid astaxanthin which is of commercial importance. Astaxanthin has a higher antioxidant activity than other intermediates of the carotenoid biosynthetic pathway. Astaxanthin acts as a quencher of free radicals and active oxygen species (Kobayashi and Sakamoto, 1999), as an enhancer of immune responses (Jyonouchi et al., 1995) and as an anticancer agent (Tanaka et al., 1994, 1995). Owing to its natural effect as potent antioxidant, astaxanthin is also employed as food supplement. It is used as food additive with colorant effect in fish farming.

Some green algae such as, for example, *Dunaliella bardawil* and *Haematococcus pluvialis* have the unique ability of accumulating carotenoids under stress conditions. In this context, it is in particular *H. pluvialis* which is suitable for the natural production of astaxanthin. *H. pluvialis* is capable of accumulating astaxanthin in amounts of up to 4% of its dry weight. This is why *H. pluvialis* plays a key role in the commercial production of astaxanthin, since the chemicosynthetic route for the production of astaxanthin is among the most complex which are commercially employed for producing an active ingredient.

The genetic transformation of green algae has been described repeatedly for *Chlamydomonas reinhardtii* and some *Chlorella* species (Kindle 1990; Lumbreras et al., 1998; Hawkins and Nakamura, 1999; Kim et al., 2002). Owing to their metabolism, these two algal species are thought to be less interesting for the natural production of carotenoids.

The genetic transformation of *H. pluvialis* has been described by Teng at al. (2003). The β-galactosidase reporter gene lacZ under the control of the SV40 promoter has been integrated into the algal genome by means of microparticle bombardment. Successfully transformed algal cells must be detected and selected individually with the aid of optical means. Algal cells which are transformed with the lacZ gene have no resistance to toxically, or dominantly, acting selection agents.

Although astaxanthin biosynthesis has been studied in detail during the last 10 years (Lu et al., 1995; Fraser et al., 1998), the production of astaxanthin by *H. pluvialis* on the large scale of the biotechnology industry remains problematic since, inter alia, cell division is inhibited during astaxanthin biosynthesis (Boussiba and von Vonshak, 1991).

It is an object of the present invention to provide a DNA vector which can be used for suitably genetically modifying the genome of eukaryotic cells, in particular of algae such as *H. pluvialis*, in order to be able to influence, or increase, the in-vivo synthesis of natural carotenoids and isoprenoids and, in particular, astaxanthin biosynthesis. It is another object of the invention to provide a vector which can be employed as dominantly-selective marker for the transformation in eukaryotic cells, in particular of algae such as *H. pluvialis*, and which makes it possible to select, in a simple manner, successfully transformed eukaryotic cells, in particular of algae such as *H. pluvialis*.

The invention achieves this object by a vector comprising (a) a DNA sequence which codes for the protein phytoene desaturase which has a resistance-conferring amino acid substitution at one position, and (b) a multiple cloning site into which any DNA sequence can be cloned.

In this context, the vectors according to the invention comprise any DNA molecules which can be used as vehicles with the aid of which foreign DNA can be introduced into a cell. They encompass cosmids, phages, viruses, YACs, BACs, more linear DNA molecules and, in particular, circular plasmids.

Within the scope of the invention, the DNA sequence of the enzyme phytoene desaturase (PDS) from *H. pluvialis* has been isolated from a genomic DNA library and sequenced (SEQ ID NO:1). The corresponding protein sequence of the *H. pluvialis* phytoene desaturase is shown in SEQ ID NO:2. The subject matter of the invention comprise all nucleic acid sequences which, taking into consideration the degeneration of the genetic code, code for the protein sequence SEQ ID NO:2.

Preferred vectors are DNA vectors in which the DNA sequence (a) which codes for the protein phytoene desaturase, the pds gene, is preferably derived from *H. pluvialis* and the resistance-conferring amino acid substitution has been introduced by means of directed mutagenesis. Especially preferred vectors are those which code for the protein *H. pluvialis* phytoene desaturase which has an amino acid substitution from leucine to arginine at position 504 of its amino acid sequence (SEQ ID NO:3).

Figure 2:
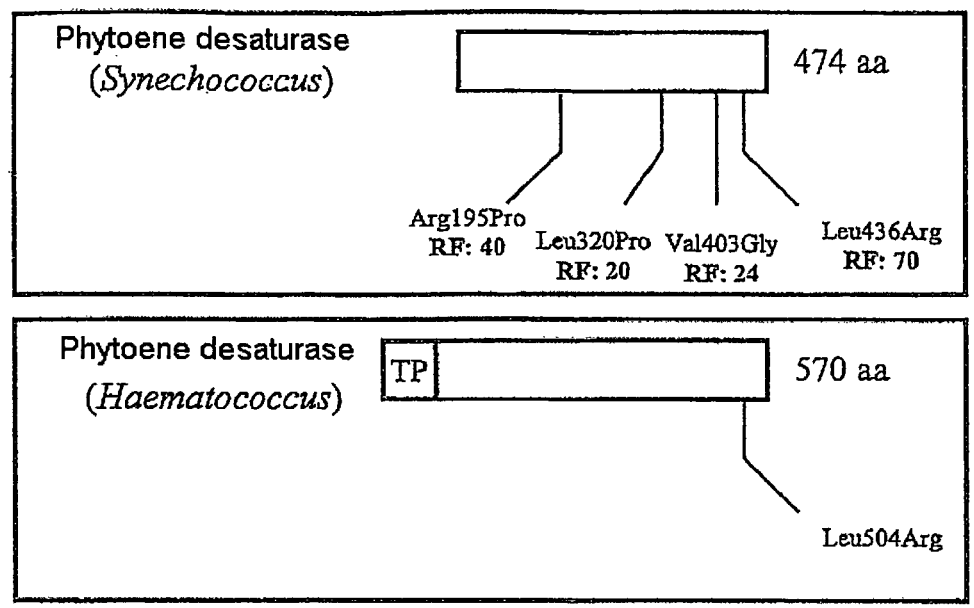

The amino acid substitution according to the invention from leucine to arginine at position 504 of the *H. pluvialis* PDS protein corresponds to the Leu437Arg substitution in *Synechococcus* PCC7942 (FIG. 2). For this purpose, the Leu codon "CTG" is replaced by the Arg codon "CGC" by directed mutagenesis. This mutation imparts, to the mutants, the highest known resistance factor to norflurazon. The resistance which has been conferred imparts, to the mutants according to the invention, a resistance to norflurazon which is up to 70-fold higher in comparison with the wild type. In accordance with the invention, norflurazon concentrations of 0.5-50 µm are used as selection substance.

Further positions in the amino acid sequence of *H. pluvialis* which are preferred for an amino acid substitution are arginine 264, leucine 388, valin 465 (FIG. 3). In *Synechococcus*, a resistance-mediating effect is known for the amino acid substitution at homologous positions.

Preferred are vectors which mediate, to transformants, a resistance to herbicides, in particular bleaching herbicides, and especially preferably norflurazon.

Within the scope of the invention, multiple cloning site (MCS), also referred to as polylinker, is understood as meaning a region in a nucleic acid sequence which has a large number of different utilizable cleavage sites for restriction endonucleases without the function of other elements of the nucleic acid sequence being adversely affected when a restriction hydrolysis takes place. Preferably, the DNA molecule is hydrolyzed only at one position by restriction endonucleases, whose cleavage sites are defined in the MCS. Examples of conventional MCSs are well known to the skilled worker from commercially available vectors and plasmids. Within the meaning of the present invention, MCS is furthermore understood as meaning any restriction cleavage site within a vector which can be used in order to clone in, into the vector sequence, any DNA sequences in a directed or undirected fashion without in the process adversely affecting other functional elements according to the invention of the vector.

An embodiment, of an MCS, which is preferred in accordance with the invention is shown in SEQ ID NO:4. In a preferred embodiment, the DNA vector according to the invention has the sequence SEQ ID NO:5 (see also FIG. 4).

The present invention preferably relates to those DNA vectors which comprise, as any DNA sequence to be cloned in, a coding sequence in the multiple cloning site.

Coding sequence is understood as meaning any DNA sequence which codes for a complete active protein or a protein fragment which has biological activity.

Especially preferred are coding sequences of plant origin. Especially preferred are furthermore coding sequences which comprise at least one promoter sequence. In this context, preferred promoters are those which make possible a constitutive transcription or expression of the coding sequences which are under their control. A preferred promoter is the β-tubulin promoter. Particularly preferred are the promoter sequences which are selected from the group consisting of *H. pluvialis* promoters of the actin gene (SEQ ID NO:6) and of the Rubisco gene (SEQ ID NO:7).

The invention furthermore relates to DNA vectors in which the coding sequence comprises a functional gene to be expressed, in addition to at least one promoter gene. Especially preferred in this context are DNA vectors which comprise a coding sequence which is selected from the group consisting of carotenoid biosynthesis genes, astaxanthin biosynthesis genes and isoprenoid biosynthesis genes. Particularly preferred are gene sequences of β-carotene ketolase, carotenoid hydroxylase, ζ-carotene desaturase, phytoene synthase, leucopene cyclase, deoxyxylulose synthase and 1-deoxy-xylose 5-phosphate reductoisomerase (Berthold et al., 2002, Hallmann and Sumper, 1996, Mahmoud and Croteau, 2001).

The invention furthermore relates -to the use of the vector according to the invention for transforming eukaryotic cells, in particular single-celled plant cells. It is especially preferred to use the vector according to the invention for the transformation of algal cells, especially. *H. pluvialis* cells. Within the scope of the invention, transformation is understood as meaning the introduction of foreign DNA into an organism.

The use of the vector according to the invention as selective marker for transformation purposes is also a subject matter of the invention. Especially preferred in this context is the use as dominant selective marker.

A selective marker within the meaning of the present invention mediates, to a transformed organism, a property by means of which this organism can be distinguished readily from untransformed organisms of the same species. A dominant-selective marker is understood as meaning a marker which mediates a property by means of which selection pressure can be exerted within the species so that, in a population of transformed and untransformed organisms of the same species, only the transformed organisms are viable. By adding norflurazon to growth media it is possible, for example, to select *H. pluvialis* cells which have been successfully transformed with the vector according to the invention of SEQ ID NO:4 from untransformed cells which are not viable under these conditions. The selection of the transformants is accomplished in accordance with the invention with norflurazon concentrations of 0.5-50 µm. The selection can be accomplished in liquid culture or by adding the herbicide to nutrient media plates.

Using mutated PDS as the first dominant selective marker for the transformation of eukaryotes, in particular algae such as *H. pluvialis*, the present invention provides an important contribution to the biotechnological utilization of eukaryotes, in particular algae such as *H. pluviadis*. For example, the vector according to the invention can be used with or without insertion of a coding sequence into the MCS in order to influence, or to modify, carotenoid biosynthesis in transformants.

The invention furthermore relates to a method of transforming eukaryotic cells using a vector according to the invention. Such transformation methods are known to the skilled worker. They comprise, for example, the use of PEG, glass beads, electroporation and micro-particle bombardment. Especially preferred in accordance with the invention is a method in which the transformation is carried out by means of particle bombardment. A preferred embodiment in this context is the particle bombardment with tungsten or gold particles 0.4 to 1.7 μm in size which have previously been coated with vector DNA according to the invention, carried out at a pressure of from 500 to 2500 psi and in vacuo. After the transformation, the cells are preferably regenerated in OHA liquid medium (2.42 g Tris-acetate pH 6.8) with shaking overnight in the dark. The cells are then plated on OHA plates under selection pressure with 0.7% strength OHA agarose. Transformants can be observed after 3-4 weeks under light-dark-intervals of equally long intervals of light (15-25 $\mu E^{*}m^{-2*}s^{-1}$) and dark (in each case 6-12 h). The transformation efficacy is approximately $1*10^{-4}$ to $10*10^{-8}$ cells/μg DNA, preferably $1*10^{-6}$ cells/μg DNA.

The invention additionally comprises a transgenic plant cell and its progeny which, after transformation with the DNA vector according to the invention, is characterized in that it features an incorporation of the introduced DNA into the nuclear genome. Preferred in this context are transgenic plant cells and their progeny which display a single or multiple incorporation of the introduced DNA into the nuclear genome. Particularly preferred are transgenic plant cells and their progeny in which the introduced gene is expressed constitutively.

SEQ ID NO:1: Nucleic acid sequence of the pds gene which codes for the protein *H. pluvialis* phytoene desaturase SEQ ID NO:2: Protein sequence of the *H. pluvialis* phytoene desaturase SEQ ID NO:3: Protein sequence of the phytoene desaturase with Leu504 Arg amino acid substitution SEQ ID NO:4: Nucleic acid sequence of the MCS of the vector Plat-pdsMod4.1 according to the invention SEQ ID NO:5: Nucleic acid sequence of the preferred DNA vector Plat-pdsMOD4.1

SEQ ID NO:6: Nucleic acid sequence comprising the actin promoter (SmaI fragment). The nucleic acid sequence comprises coding regions with introns, exons and the promoter sequence, which is indicated (–).

SEQ ID NO:7: Nucleic acid sequence comprising the rbsc promoter (Rubisco small subunit) (PstI fragment). The nucleic acid sequence comprises coding regions with introns, exons and the promoter sequence, which is indicated.

FIG. 1: Carotenoid biosynthetic pathway of geranylgeranyl diphosphate to astaxanthin FIG. 2: Comparison of phytoene desaturase from *Synechococcus* and *H. pluvialis* with known mutations and resistance factors (RF) to norflurazon FIG. 3: Amino acid sequence alignment of the PDS proteins from *H. pluvialis* and *Synechococcus*. Positions preferred for an amino acid substitution imparting resistance to norflurazon are indicated.

Figure 4:
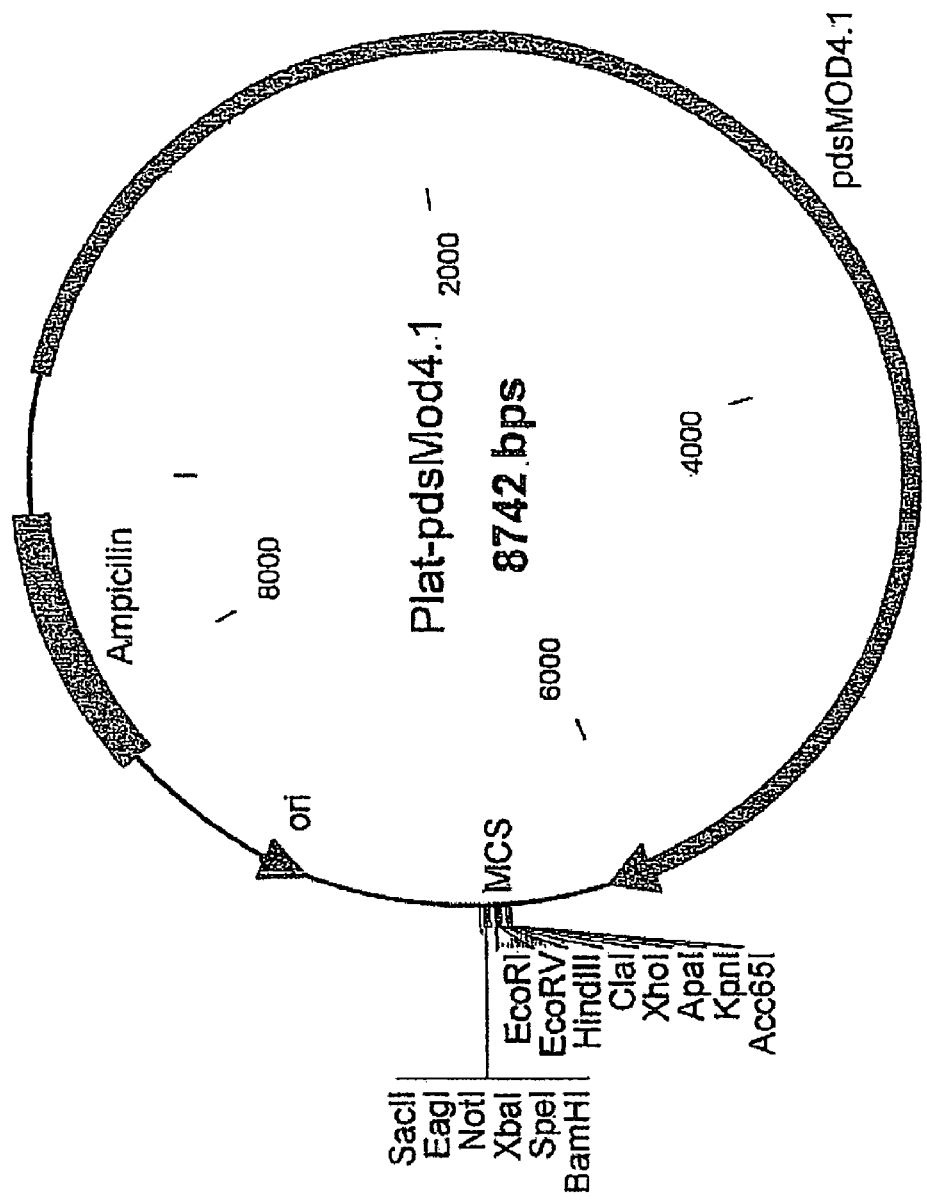

FIG. 4: Plasmid mark of the vector Plat-pdsMod4.1; MCS (multiple cloning site), on (origin of replication)

Figure 5:
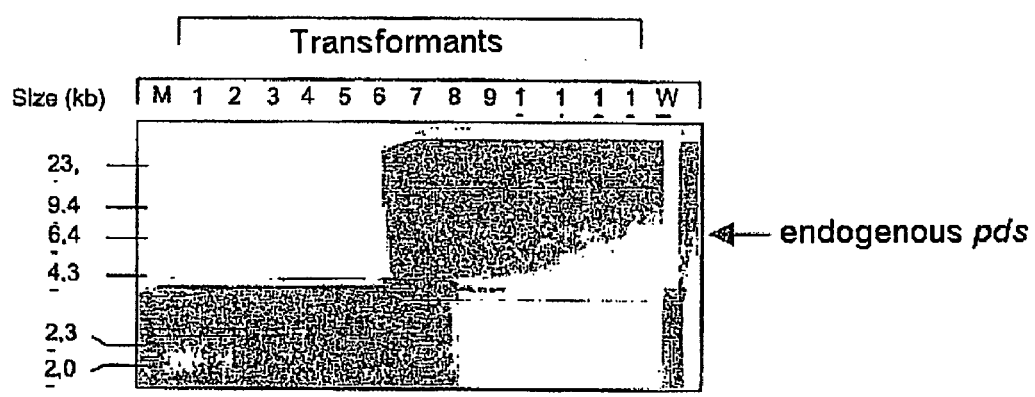

FIG. 5: Southern blot of genomic DNA after digestion with XbaI and XhoI, and detection via phytoene desaturase probe. Marker (M) in kilobases (kb)

Figure 6:
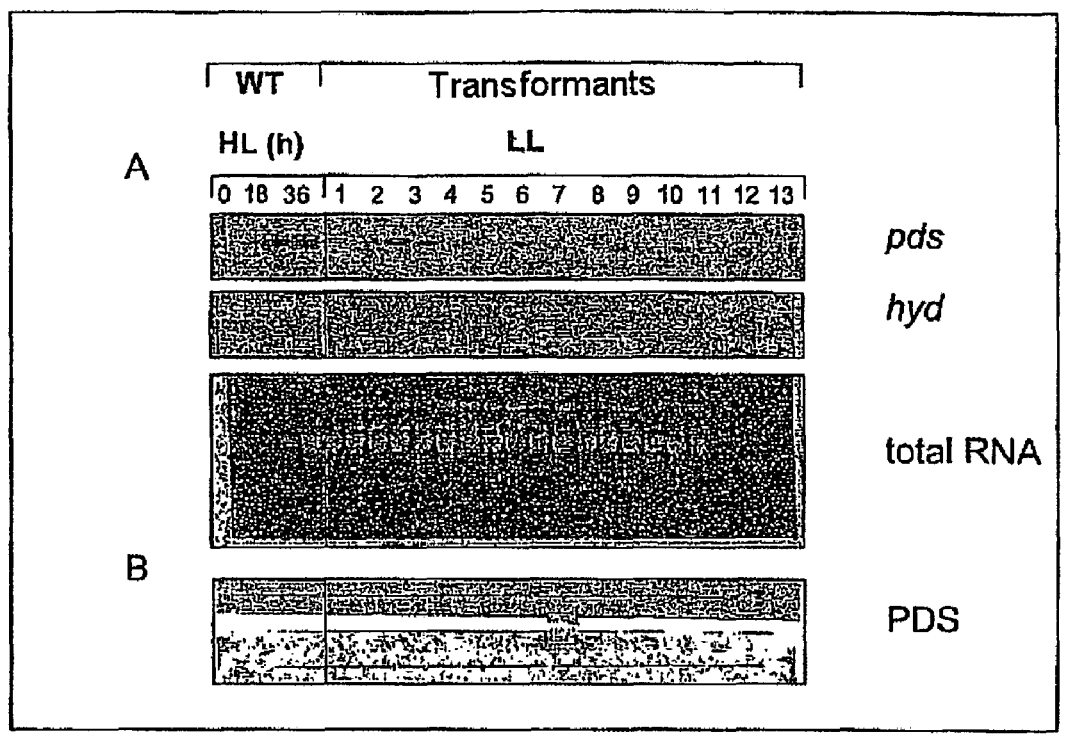

FIG. 6: (A) Northern blot of three WT strains put under continuous high light stress ($120\,\mu E^{*}m^{-2*}s^{-1}$) (WT 0, 18 and 36 hours) and the transformants P1-P13. (B) Western blot with antibodies against the phytoene desaturase protein. The band migrates at the level of the calculated 55 kDa. Phytoene desaturase mRNA (pds), carotenoid hydroxylase mRNA (hyd), phytoene desaturase protein (PDS).

Figure 7:
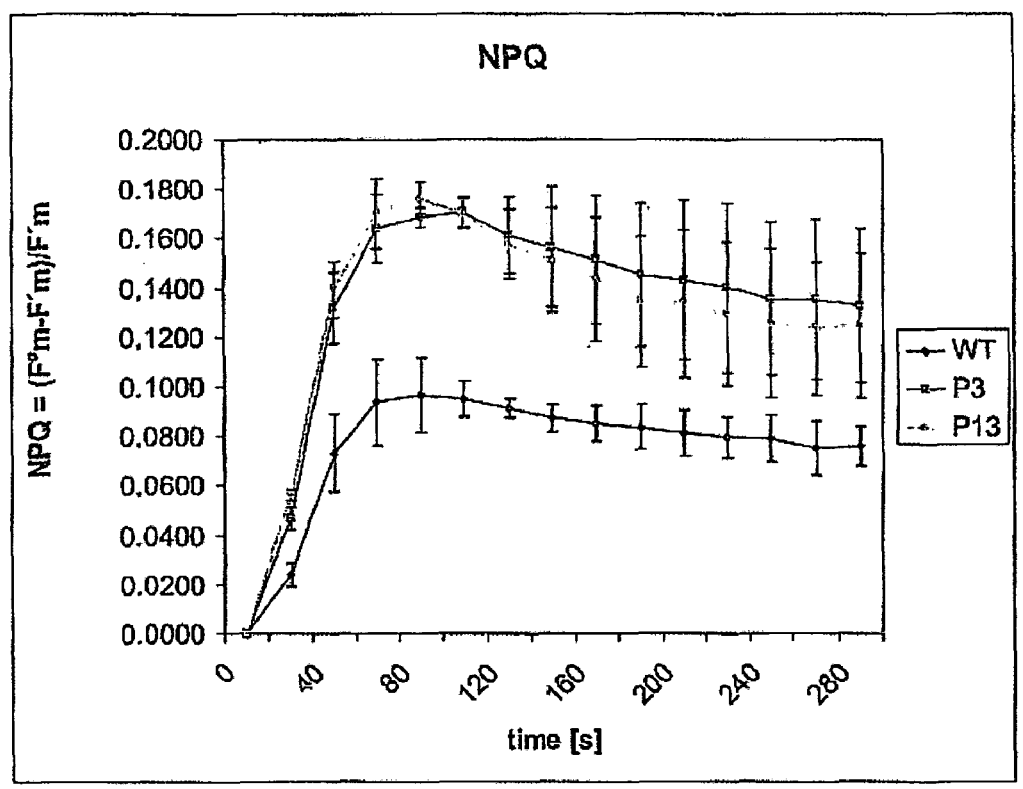

FIG. 7: Representation of the nonphotochemical quenching (NPQ). NPQ=$(F^{\circ}_{m}-F'_{m})/F'_{m}$ $F^{\circ}_{m}$ is the maximum fluorescence of dark-adapted organisms after a saturating light pulse. $F'_{m}$ maximum fluorescence after saturating light pulses in defined intervals at 20 s.

Figure 8:
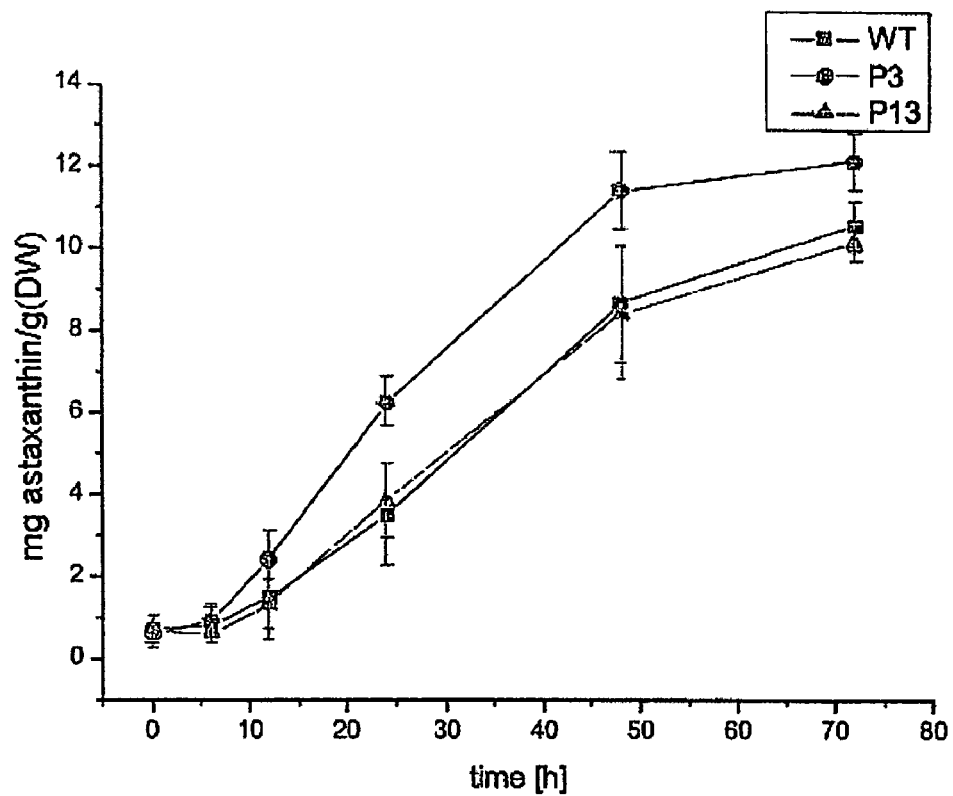

FIG. 8: Representation of the accumulation of the keto carotenoid astaxanthin in the WT *H. pluvialis* and two transformants (P3, P13) without added herbicide under continuous high light (175 $\mu Em^{-2}\,s^{-1}$). Dry weight (DW), time in hours (h).

Figure 9:
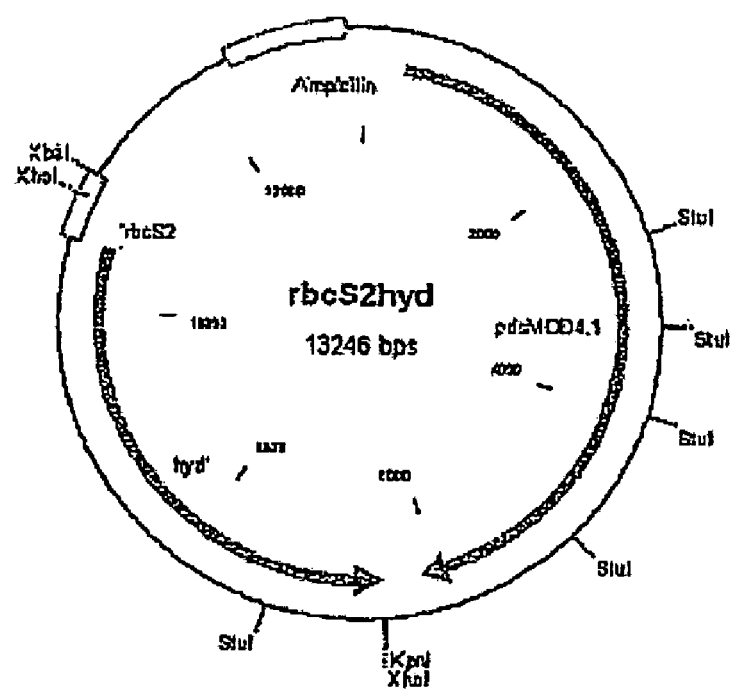

FIG. 9: Transformation vector for the constitutive expression of the hydroxylase gene (hyd) under the control of the promoter of the small Rubisco subunit (rbcS2)

EXAMPLES

Preparation of the Transformation Vector for the Transformation of *H. pluvialis*

A portion of the phytoene desaturase 6.1 kilobases in size was isolated from a genomic DNA library of *H. pluvialis* and subcloned into the multiple cloning site (MCS) of the pBluescriptSK vector (stratagene) via the restriction cleavage sites XbaI and XhoI. A nucleotide substitution from CTG to CGC was carried out via directed mutagenesis with the primers PDS-Qmut-plu2 CCA AGC AGA AGT ACC GCG CCT CCA TGG AGG G (SEQ ID NO: 8) and PDS-Qmut-min2 CCC TCC ATG GAG GCG CGG TAC TTC TGC TTG G (SEQ ID NO: 9); the plasmid was named pPDS-Q2. This nucleotide substitution led to an amino acid substitution from leucine to arginine in codon 504 (FIG. 2), and confers to mutants a resistance to norflurazon.

Starting from the plasmid pPDS-Q2, the terminal restriction cleavage sites XbaI and XhoI were eliminated by PCR with the specific primers, and two new EcoRV cleavage sites were introduced. Via these restriction cleavage sites, the mutated phytoene desaturase gene was subcloned into an NaeI cleavage site of a pBluescriptSK vector. The multiple cloning site (SEQ ID NO:4) of the vector is thereby free for other cloning steps. The transformation platform thus prepared was named Plat-pdsMod4.1 (FIG. 4).

Transformation of *H. pluvialis* with the Transformation Vector Plat-pdsMod4.1

*H. pluvialis* cells were grown for 4 days in liquid medium under standard conditions (light-dark-rhythm of 12 hours light ($20\,\mu E^{*}m^{-2*}s^{-1}$) and 12 hours dark) up to a cell density of $3.5*10^5$ cells/ml (Kobayashi, Kakizono et al., 1991). The cells were centrifuged for 5 minutes at 16° C. and 4000×g, resuspended and in each case $1*10^8$ cells were plated onto nylon filters (Roche). The filters were transferred to OHM medium plates (Fabregas, Dominguez et al., 2000) and dried until transformation was performed. The tungsten particles which were 0.4-1.7 μm in size were coated with 2 μg of Plat-pdsMod4.1 vector DNA following the protocol of Klein and its coworkers (Klein, Wolf et al., 1987). The particle gun PDS-1000/He from Bio-Rad was used for the transformation at a pressure of 1350 psi and a vacuum of 25 mmHg. Otherwise, the standard settings were retained.

After the transformation, the cells were regenerated on the nylon filter in OHA liquid medium (2.42 g Tris-acetate PH 6.8) overnight with gentle shaking in the dark. Thereafter, the cells were briefly centrifuged and plated with 0.7% OHA top agarose onto 10 to 20 OHA plates (5 μm norflurazon). The first transformants were observed after a growth phase of three to four weeks under a light-dark rhythm of 12 hours light ($20\,\mu E^{*}m^{-2*}s^{-1}$) and 12 hours dark. The transformation efficacy is approximately $1*10^{-8}$ cells/μg DNA.

Molecular Analyses of the Cells Transformed with the Vector Plat-pdsMod4.1

The positive transformants were inoculated repeatedly onto OHA plates with a norflurazon concentration of 0.7 µM. At these concentrations, the growth of the WT cells is greatly inhibited. The transformants were grown in liquid medium with a norflurazon concentration of 3 µM in order to subject the transformants to molecular analysis via Southern, Northern and Western blot analyses.

Southern Blot, Verification of the Integration of the Transformation Plasmid in the Genome of *H. pluvialis*

After four days' growth under standard conditions at a norflurazon concentration of 3 µM in liquid medium, the cells were isolated by centrifugation, and the genomic DNA was isolated from the various transformants and several WT controls. The genomic DNA obtained was digested with the restriction enzymes XbaI and XhoI and separated on an 0.8% strength agarose gel. The DNA was blotted by standard methods and hybridized with a probe for PDS (FIG. 5).

The Southern blot clearly reveals the endogenous phytoene desaturase at approximately 5.9 kb in all transformants and in WT. The additionally integrated mutated phytoene desaturases migrate in all cases further up than the endogenous phytoene desaturase. It is known from other organisms such as, for example, the fungus *Neurospora crassa* that vectors frequently integrate into the genome in the form of tandem repeats (Cogoni and Macino 1997). This phenomenon explains the very pronounced bands in transformants P6, 7, 11 and P13. the genomic DNA was additionally also hybridized with a probe for the ampicillin resistance cassette of the transformation vector Plat-pdsMod4.1. Under these conditions, several pronounced bands were visible in all cases, with the exception of the transformant P3.

Northern and Western Blot Analyses of the Transformants P1-P13

After four days' growth under standard conditions at a norflurazon concentration of 3 µM in liquid medium, the cells were isolated by centrifugation, and the RNA was isolated from the various transformants and several WT controls. For the further analysis of the transformants' transcription patterns, the RNA samples were separated on a 1% denaturing agarose gel, blotted, and hybridized with a probe for the phytoene desaturase mRNA (pds) and for the carotenoid hydroxylase mRNA (hyd) (FIG. 6A). The hydroxylase acts as internal standard in order to allow statements on the transformants' stress status. Hydroxylase is induced under stress conditions such as stress caused by light or salt and is otherwise below the detection limit (Steinbrenner and Linden 2001; Steinbrenner and Linden 2003).

To obtain protein samples, the cells were likewise harvested after four days' growth under standard conditions and separated on a 12.5% strength SDS polyacrylamide gel. The phytoene desaturase protein was detected with a specific antibody (Grunewald, Eckert et al., 2000).

The WT cells which have been placed under continuous high light conditions (120 µE*m$^{-2}$*s$^{-1}$) show, for phytoene desaturase (pds) a basal expression of the pds gene at the point in time of induction (0 hours). This signal increases in the course of 18 hours. The carotenoid hydroxylase's behavior under these induction conditions is adequate, the transcription is somewhat delayed.

The expression patterns of the phytoene desaturase mRNA of the transformants P1, P2, P5 and P6 are comparable with the basal expression of the WT at 0 hours under standard conditions. Indeed, the expression levels for the transformants P8, P9 and P10 are somewhat below the level of the basal expression of the WT at 0 hours. In two further independent Northern blot analyses, the expression of the transformants P8, P9 and P10 corresponded to the basal expression of the WT at 0 hours. Here, the transformants P3, P4, P7, P11, P12 and P13 show an elevated transcription level which, in comparison with the continuous high light control is between 0 hour and 18 hours; this was also observed in two further independent Northern blot analyses. In this case, the increase cannot be attributed to induction as a result of stress, but to the multiple incorporation of the transformation vector Plat-pds-Mod4.1 in the genome of *H. pluvialis*. The expression of carotenoid hydroxylase as stress control shows no increased transcription level under these standard conditions.

In the Western blot with an antibody against PDS, the protein amount increases uniformly up to the 36-hour-value (FIG. 6B).

The protein quantities of all transformants are slightly above the 0 hour value of the WT control. The protein quantities of transformants P3, P5, P7, P11 and P13 are again increased over the other levels and comparable with the protein quantity of the WT 18-hour-value under continuous high light conditions. The higher transcription levels of phytoene desaturase can also be observed at the protein level in transformants P3, P7, P11 and P13.

Physiological Studies of the Plat-pdsMod4.1 trans-Formants Determination of the Nonphotochemical Quenchings (NPQ) of the Plat-pdsMod4.1 Transformants Some higher plants with modified carotenoid biosynthesis have been studied in greater detail in the past. Thus, tobacco has been transformed with the phytoene desaturase gene crtl from *Erwinia uredovora* (Misawa, Yamano et al., 1993). In one of the resulting transformants, named ET4-208, a higher resistance to norflurazon was observed. Later, a modified carotenoid composition in the transgenic crtl plants in comparison with untransformed controls has also been detected (Misawa, Masamoto et al., 1994).

A possibility of studying modifications in the carotenoid composition in transgenic plants is measuring the chlorophyll fluorescence. Firstly, this is a very rapid method of screening photosynthetic mutants; secondly, a modification of the xanthophyll contents is reflected in the chlorophyll fluorescence (Niyogi, Bjorkman et al., 1997).

The various transformants were grown for three to four weeks on OHA plates without norflurazon under standard conditions. Prior to the measurements, the plates were dark-adapted for 24 hours. Using a PAM fluorimeter (Walz, Germany), the chlorophyll fluorescence of all transformants was measured, and the NPQ was calculated via the following formula: NPQ=$(F°_m-F'_m)/F'_m$ $F°_m$ is the maximum fluorescence of the dark-adapted organisms after a saturating light pulse. $F'_m$ is the maximum fluorescence after saturating light pulses in defined intervals; in our case, the intervals were 20 s. A good review article on this subject was written by Kate Maxwell and Giles N. Johnson (Maxwell and Johnson 2000).

All of the transformants measured, with the exception of P3 and P13, showed fluorescence curves and NPQ curves like the wild type (WT). The NPQ of transformants P3 and P13 is approximately 50% higher over the entire duration of the measurement than in the case of the WT (FIG. 7).

Comparison of the Distribution of the Pigmented Carotenoids in the WT *H. pluvialis* and of Three Transformants without Added Herbicide The transformants were grown for four days under standard conditions in liquid medium without added herbicide, and the cells were isolated by centrifugation and the pellets were freeze-dried. The dry weights of the pellets were determined and the cells were comminuted in a mortar with addition of methanol. The chlorophylls were measured photometrically and later hydrolyzed by addition of 6% strength KOH. The carotenoids were extracted in petroleum ether/ether (b.p. 35° C.-60° C.) (9:1 v/v), the mixtures were evaporated and the residues were taken up in 100% strength acetone. The samples were then separated via an HPLC column.

TABLE 1

HPLC analysis of the total pigment extract of
H. pluvialis WT and the phytoene desaturase transformants
P1, P3 and P13. Percentage distribution of the
carotenoids of the total carotenoid.

| | H. pluvialis WT | Transformant P1 | Transformant P3 | Transformant P13 |
|---|---|---|---|---|
| Neoxanthin | 9.6 | 9.6 | 12.9 | 8.9 |
| Violaxanthin | 8.6 | 8.3 | 11.7 | 11.23 |
| Lutein | 65.3 | 62.9 | 65.8 | 64 |
| β-Carotene | 16.6 | 19 | 9.6 | 15.7 |

As can readily be seen from table 1, the percentage distribution of the individual carotenoids in the WT and transformant P1 is very similar. In comparison, the carotenoid compositions in transformants P3 and P13 have changed drastically. In P3, the xanthophylls are increased by approximately 6% and the β-carotene content is reduced by this value in comparison with the WT. In transformant P13, the violaxanthin content is increased by approximately 3%. Zeaxanthin, which is directly involved in the NPQ process, cannot be measured under standard conditions. This would require HPLC measurements of cells which have been subjected to high light stress. However, the increase in the violaxanthin contents of approximately 3% of transformants P3 and P13 still permits a direct coupling with the increased NPQ of these transformants since the violaxanthin pool under high light conditions is converted into zeaxanthin.

Carotenoid Composition of the H. pluvialis Transformants P3, P13 and WT Under Low Light Conditions It is known that the heterologous expression of the pds gene from Erwinia uredovora in tobacco modifies the carotenoid composition in the leaf (Misawa et al., (1994)). The analysis of norflurazon-resistant Synechococcus mutants confirmed that it is the phytoene desaturation in carotenoid biosynthesis which is the rate-limiting step in cyano bacteria (Chamovitz et al., (1993)). To confirm these results, the P3, P13 and WT H. pluvialis transformants were grown under low light conditions, and all carotenoids were extracted. None of the transformants studied showed altered carotenoid quantities in comparison with the dry weight. A subsequent HPLC analysis of the carotenoid composition in transformants P3, P13 and WT revealed, for transformant P3, a slightly increased amount of xanthophylls violaxanthin, whereas the amounts of lutein and neoxanthin were slightly reduced.

Comparison of the Accumulation of the Keto Carotenoid Astaxanthin in the WT H. pluvialis and Transformants P3 and P13 without Added Herbicide Under Continuous High Light To carry out the high light experiments, the H. pluvialis cells were grown for 4 days under standard conditions. After this period, the light intensity was increased from 20 $\mu Em^{-2} s^{-1}$ to 175 $\mu Em^{-2} s^{-1}$ and the light/dark rhythm to 24 hours continuous light. At certain times after the induction (0, 6, 12, 24, 48, 72 hours), samples were taken and centrifuged.

Carotenoids were extracted as described by Boussiba et al., (1992). In this manner, the dry weight (DW) of the freeze-dried cells was determined, and the material was again comminuted in a mortar with addition of seesand, 30% methanol and 5% KOH. After hydrolysis of the chorophylls for 10 minutes at 70° C., the samples were centrifuged for 5 minutes at 4000 rpm, and the chlorophyll-containing supernatant was discarded. The pellet was taken up in 100% DMSO (dimethyl sulfoXide) and heated for 10 minutes at 70° C. This extraction step was repeated until the pellet had lost its reddish color. Astaxanthin and its esters have their main absorption maximum at 492 nm. However, a measurement of this wavelength was not carried out since the total carotenoids (mainly β-carotene, lutein and violaxan-thin) too showed absorption in this wavelength range. With the aid of an astaxanthin standard (Sigma, in 100% DMSO), a calculation factor was thus determined which permitted the determination of the astaxanthin content in a wavelength range (550 nm) in which the total carotenoids no longer absorbed. Thus, the absorption of the astaxanthin standard was only measured at a wave-length of 492 nm ($A_{492}$) and subsequently at a wavelength of 550 nm, ($A_{550}$). The absorption values were measured at 550 nm and then multiplied by the quotient $A_{492}/A_{550}=3.2$, and the astaxanthin content was calculated with an astaxanthin absorption coefficient (E1%/1 cm=2220) using the formula of Davies (1976).

Six hours after changing the light conditions, no astaxanthin was detectable as yet (FIG. 8). After 8 hours' exposure to high light, the transformant P3 showed a visibly red phenotype, while the WT and the other transformants remained green. 12 hours after induction, the amount of astaxanthin formed in the WT and in transformant P13 amounted to 1.47 mg/g DW and 1.32 mg/g DW; in contrast, the value which the transformant P3 had reached was 2.37 mg/g DW. After 24 hours, the astaxanthin quantity measured, of the WT and of the transformant P13, was 3.48 mg/g DW and 3.79 mg/g DW, respectively. At this point in time, transformant P3 showed an approximately 40% increase with an astaxanthin quantity of 6.22 mg/g DW in relation to the wild type. After 48 hours under continuous high light, the WT and the P13 transformant showed values of 8.6±1.4 mg/g DW and 8.4±1.6 mg/g DW, respectively. An astaxanthin accumulation which was increased by 26% in comparison with the WT and P3 was determined for the transformant P3 after 48 hours (11.4±0.9 mg/g DW). 72 hours after continuous light stress, the WT and the P13 transformant revealed an amount of 10.5 mg/g DW and 10.1 mg/g DW, respectively, with the transformant P3, with a value of 12.1 mg/g DW, showing an astaxanthin accumulation which was 14% higher.

Thus, the transformant P3 differed greatly in comparison with the transformant P13 and the WT with regard to its accumulation of astaxanthin under continuous high light. During the continuous-light experiment, P3 showed an increase in the astaxanthin quantities by approximately 40% after 24 hours, in comparison with the WT. This difference drops to 26% after 48 hours and reaches a value of 14% after 72 hours.

The results demonstrate that the phytoene desaturation step in H. pluvialis is rate-limiting under high light conditions, but not under low light conditions.

Increasing Astaxanthin Biosynthesis by using β-carotene Ketolase Under the Control of Constitutive Promoters Vector Construction and Transformation Using the transformation platform Plat-pdsMod4.1, transformation plasmids with promoters of the actin gene or of ribulose bisphosphate carboxylase followed by a cloning site for various restriction endonucleases were prepared; both promoters were isolated from a genomic DNA library. These platforms furthermore comprise the 3'-untranslated region of the respective genes, which also act as polyadenylation signal for introduced cDNAs. The cDNAs of carotenoid hydroxylase and of β-carotene ketolase were amplified via PCR and provided with terminal restriction cleavage sites. This made it possible to introduce these cDNAs in-frame into the transformation platform. The constructs in question were also prepared for genomic DNA of the two carotenoid biosynthesis genes. FIG. 9 shows a transformation vector for the constitutive expression of the hydroxylase gene under the control of the small Rubisco subunit promoter.

Three constructs under the control of an actin promoter with different translation starts, and in each case one construct under the control of the Rubisco promoter, were cloned, and transformed into *H. pluvialis*, for the cDNAs and the genomic hydroxylase sequences. The selection pressure was lowered by reducing the norflurazon concentration from 5 µM to 3 µM. This was intended also to obtain transformants which, on the one hand, have a lower resistance to norflurazon, but whose chances of growth, on the other hand, were reduced as the result of a shift of the metabolic equilibrium toward zeaxanthin or canthaxanthin. A shift of this equilibrium might mean, for example, a reduced formation of lutein, which plays an important role in the association of antenna complexes in the thylakoid membrane. The formation of the chlorophylls, or else the formation of tocopherols, might also be affected by such a shift, since those substances also diverge from the very early isoprenoid biosynthesis.

Selection of Transformants

Following transformation, the colonies obtained were transferred to other medium plates comprising norflurazon. Thereafter, 15 transformants of each construct were transferred into liquid medium under very low selective pressure.

After a further growth phase, where none of the transferred transformants showed a pronounced carotenoid accumulation of canthaxanthin or zeoxanthin, the cells were placed under high light (120 µE*m$^{-2*}$s$^{-1}$) for 24 hours.

The transformants which have been transformed with the hydroxylase constructs of genomic DNA under the control of the Rubisco promoter (Plat-rbcS2gHyd) and of the second actin promoter (Plat-ActPII-gHyd) (second translation start with an intron) showed no reddish-brown colored cells in comparison with the transformants of the other hydroxylase constructs.

In the case of the ketolase construct transformants, those which had been transformed with the cDNA and the ketolase gene under the control of the second actin promoter (Plat-ActPIIgBkt and Plat-ActPIIcBkt) (second translation start with an intron) were subjected to further studies.

Southern Blot and Northern Blot Analyses of the Hydroxylase Constructs 10 among the in each case 15 pre-screened transformants were selected and grown on for molecular-biological studies. After the genomic DNA of the individual transformants had been isolated, they were subjected to restriction digestion and separated on an agarose gel, blotted and hybridized with a probe for hydroxylase. Among the 10 transformants which were under the control of the second actin promoter (Plat-ActPII-gHyd), two transformants unambiguously revealed additional hydroxylase copies in the genome. Among 10 transformants under the control of the Rubisco promoter (Plat-rbcS2gHyd), 6 were positive with additional copies in the genome. Reducing the norflurazon concentration on the selection plates in order to favor growth-disadvantaged transformants clearly has a negative effect on the selection.

The RNA of the remaining transformants was extracted and separated on a denaturing agarose gel, blotted and hybridized with a probe for the hydroxylase mRNA. Two of the transformants showed an increased transcript level of hydroxylase mRNA. Control experiments with other probes for carotenoid biosynthesis genes β-lycopene cyclase and phytoene synthase also revealed an increased transcript level in these two transformants.

REFERENCES

1. Teng, C., Qin, S., Liu, J., Yu, D., Liang, C. and Tseng, C. 2002. Transient expression of lacZ in bomarded unicellular green alga *Haematococcus pluvialis*. Journal of Applied Phycology 14: 495-500.
2. Boussiba, S. and Vonshak, A. 1991. Astaxanthin accumulation in the green alga *Haematococcus pluvialis*. Plant Cell Physiol. 32: 1077-1082.
3. Fraser, P. D., Shimada, H. and Misawa, N. 1998. Enzymic confirmation of reactions involved in routes to astaxanthin formation, elucidated using a direct substrate in vivo assay. Eur. J. Biochem. 252: 229-236.
4. Hawkins, R. L. and Nakamura, M. 1999. Expression of human growth hormone by the eukaryotic alga, *Chlorella*. Curr. Microbiol. 38: 335-341.
5. Jyonouchi, H., Sun, S. and Gross, M. 1995. Effect of carotenoids on in vitro immunoglobulin production by human peripheral blood mononuclear cells; astaxanthin, a carotenoid without vitamin A activity, enhances in vitro immunoglobulin production in response to a T-dependent stimulant and antigen. Nutr. Cancer 23: 171-183.
6. Kim, D. H., Kim, Y. T., Cho, J. J., Bae, J. H. and Hur, S. B. 2002, Stable integration and functional expression of flounder growth hormone gene in transformed micro alga *Chlorella ellipsoidea*. Marine Biotech. 4: 63-73.
7. Kindle, K. L. 1990. High-frequency nuclear transformation of *Chlamydomonas reinhardii*. Proc. Natl. Acad. Sci. USA 87: 1228-1232.
8. Kobayashi, M. and Sakamato, Y. 1999. Singlet oxygen quenching ability of astaxanthin esters from the green alga *Haematococcus pluvialis*. Biotech. Lett. 21: 265-269.
9. Lu, E. Vonshak, A., Gubbay, R., Hirschberg, J. and Boussiba, S. 1995. The biosynthetic pathway of astaxanthin in a green alga *Haematococcus pluvialis* as induced by inhibition with diphenylamine. Plant Cell Physiol. 36: 1519-1524.
10. Lumbreras, V., Stevens, D. R. and Purton, S. 1998. Efficient foreign gene expression in *Chlamydomonas reinhardii* mediated by an endogenous intron. Plant J. 14: 441-447.
11. Tanaka, T., Makita, H., Ohnishi, M., Mori, H., Satoh, K. and Hara, A. 1995. Chemoprevention of mouse urinary bladder carcinogenesis by the naturally occurring carotenoids astaxanthin. Carcinogenesis 15: 15-19.
12. Chamovitz, D., Sandmann, G. and Hirschberg, J. 1993. Molecular and biochemical characterization of herbicide-resistant mutants of cyanobacteria reveals that phytoene desaturation is a rate-limiting step in carotenoid biosynthesis. The Journal of Biological Chemistry, Vol. 268, No. 23, p. 17348-17353.
13. Martinez-Férez, I., Vioque, A. and Sandmann, G. 1994. Mutagenesis of an amino acid responsible in phytoene desaturase from *Synechocystis* for binding of the bleaching herbicide norflurazon. Pesticide Biochemistry and Physiology 48: 185-190.
14. Martinez-Férez, I. M. and Vioque, A. 1992. Nucleotide sequence of the phytoene desaturase gene from *Synechocystis* sp. PCC 6803 and characterization of a new mutation which confers resistance to the herbicide norflurazon. Plant Molecular Biology 18: 981-983.
15. Linden, H., Sandmann, G., Chamovitz, D., Hirschberg, J. and Boger, P. 1990. Biochemical characterization of *Syn-* echococcus mutants selected against the bleaching herbicide norflurazon. Pesticide Biochemistry and Physiology 36: 46-51.
16. Sandmann, G., Schneider, C. and Boger, P. 1996. A new non-radioactive assay of phytoene desaturase to evaluate bleaching herbicides. Verlag der Zeitschrift für Naturforschung. 51c: 534-538.
17. Bartley, G. E., Vitanen, P. V., Pecker, I., Chamovitz, D., Hirschberg, J. and Scolnik, P. 1991. Molecular cloning and expression in phytosynthetic bacteria of a soybean cDNA coding for phytoene desaturase, an enzyme of the carotenoid biosynthesis pathway. Proc. Natl. Acad. Sci. USA 88: 6532-6536.
18. Chamovitz, D:, Pecker, I. and Hirschberg, J. 1991. The molecular basis of resistance to the herbicide norflurazon. Plant Molec. Biol. 16, 967-974.
19. Berthold, P., Schmitt, R., Mages, W. (2002). "An engineered Streptomyces hygroscopicus aph 7" gene mediates dominant resistance against hygromycin B in *Chlamydomonas reinhardtii*. "Protist. 153(4): 401-12.
20. Chamovitz, D., Sandmann, G., Hirschberg, J. (1993) "Molecular and biochemical characterization of herbicide-resistant mutants of cyanobacteria reveals that phytoene desaturation is a rate-limiting step in Carotenoid Biosynthesis, J. Biol. Chem. 268: 17348-17353.
21. Boussiba, S., Fan, L. and Vonshak, A. (1992) Enhancement and determination of astaxanthin cumulation in green alga *Haematococcus pluvialis*. In Packer, L. (ed.) Methods in Enzymology. Academic Press, London, Vol. 213, pp. 371-386.
22. Cogoni, C. and G. Macino (1997). "Isolation of quelling-defective (qde) mutants impaired in post-transcriptional transgene-induced gene silencing in *Neurospora crassa*." Proc. Natl. Acad. Sci. USA 94(19): 10233-8.
23. Davies, B. H. (1976) Carotenoids. In Goodwin, T. W. (ed.) Chemistry and Biochemistry of Plant Pigments. Academic Press, London, pp. 38-165.
24. Fabregas, J., A. Dominguez, et al. (2000). "Optimization of culture medium for the continuous cultivation of the microalga *Haematococcus pluvialis*. "Appl. Microbiol. Biotechnol. 53(5): 530-5.
25. Fraser, P. D., S. Romer et al. (2002). "Evaluation of transgenic tomato plants expressing an additional phytoene synthase in a fruit-specific manner. "Proc. Natl. Acad. Sci. USA 99(2): 1092-7.
26. Grunewald, K., M. Eckert, et al. (2000). "Phytoene desaturase is localized exclusively in the chloroplast and up-regulated at the mRNA level during accumulation of secondary carotenoids in *Haematococcus pluvialis* (Volvocales, chlorophyceae)." Plant Physiol. 122(4): 1261-8.
27. Hallmann, A., Sumper, M. (1996). "The *Chlorella* hexose/H+ symporter is a useful selectable marker and biochemical reagent when expressed in Volvox. "Proc. Natl. Acad. Sci. USA 93(2): 669-73.
28. Klein, T. M., E. D. Wolf, et al. (1987). "High-velocity microprojectiles for delivering nucleic acids into living cells." Nature (327): 70-73.
29. Kobayashi, M., T. Kakizono, et al. (1991). "Astaxanthin Production by a Green Alga, *Haematococcus pluvialis* Accompanied with Morphological Changes in Acetate Media." J. Ferment. and Bioeng. 71(5): 335-339.
30. Mahmoud, S. S., Croteau, R. B. (2001). "Metabolic engineering of essential oil yield and composition in mint by altering expression of deoxyxylulose phosphate reductoisomerase and menthofuran synthase." Proc. Natl. Acad. Sci. USA 98(15): 15-20.
31. Maxwell, K. and G. N. Johnson (2000). "Chlorophyll fluorescence—a practical guide." J of Experim. Bot. 51(345): 659-668.
32. Misawa, N., S. Yamano, et al. (1993). "Functional expression of the *Erwinia uredovora* carotenoid biosynthesis gene crtI in transgenic plants showing an increase of beta-carotene biosynthesis activity and resistance to the bleaching herbicide norflurazon." Plant J 4(5): 833-40.
33. Misawa, N., K. Masamoto, et al. (1994). "Expression of *Erwinia phytoene* desaturase gene not only confers multiple resistance to herbicides interfering with carotenoid biosynthesis but also alters xanthophyll metabolism in transgenic plants." Plant J 6(4): 481-489.
34. Niyogi, K. K., O. Bjorkman, et al. (1997). "*Chlamydomonas* Xanthophyll Cycle Mutants Identified by Video Imaging of Chlorophyll Fluorescence Quenching." Plant Cell 9(8): 1369-1380.
35. Pecker, I., Chamovitz, D., Linden, H., Sandmann, G., Hirschberg, J. (1992). "A single polypeptide catalyzing the conversion of phytoene to zeta-carotene is transcriptionally regulated during tomato fruit ripening." Proc. Natl. Acad. Sci. USA 89(11): 4962-6.
36. Steinbrenner, J. and H. Linden (2001). "Regulation of two carotenoid biosynthesis genes coding for phytoene synthase and carotenoid hydroxylase during stress-induced astaxanthin formation in the green alga *Haematococcus pluvialis*." Plant Physiol. 125(2): 810-7.
37. Steinbrenner, J. and H. Linden (2003). "Light induction of carotenoid biosynthesis genes in the green alga *Haematococcus pluvialis*: regulation by photosynthetic redox control." Plant Mol. Biol. 52(2): 343-56.
38. Tanaka, T., Morishita, Y., Suzui, M., Kojima, T., Okumura, A., Mori, H. (1994). "Chemoprevention of mouse urinary bladder carcinogenesis by the naturally occurring carotenoid astaxanthin." Carcinogenesis 15: 15-19.
39. Tanaka, T., Kawamori, T., Ohnishi, M., Makita, H., Mori, H., Satoh, K., Hara, A. (1995). "Suppression of azoxymethane-induced rat colon carcinogenesis by dietary administration of naturally occurring xanthophylls astaxanthin and canthaxanthin during the postinitiation phase." Carcinogenesis. 16(12): 2957-63.

The invention claimed is:

1. An isolated expression vector which comprises:
   (i) a nucleic acid molecule encoding the amino acid sequence of SEQ ID NO: 2 with one of the following amino acid modifications: a modification at amino acid 504, changing leucine to arginine; a modification at amino acid 264, changing arginine to proline; a modification at amino acid 388, changing leucine to proline; a modification at amino acid 465, changing valine to glycine, wherein said nucleic acid molecule encodes a modified phytoene desaturase, which confers disease resistance, and (ii) a multiple cloning site which permits cloning of an additional nucleic acid molecule into said vector.

2. The expression vector of claim 1, further comprising a nucleic acid molecule which confers resistance to herbicides when said vector is inserted into a transformant.

3. The expression vector of claim 2, wherein said herbicide is a bleaching herbicide.

4. The expression vector of claim 3, wherein said bleaching hebicide is norflurazin.

5. The expression vector of claim 1, further comprising a nucleic acid molecule which encodes a protein at said multiple cloning site.

6. The expression vector of claim 5, wherein said nucleic acid molecule is identical to a nucleic acid molecule found in a vegetable.

7. The expression vector of claim 5, further comprising a promoter sequence.

8. The expression vector of claim 5, wherein said promoter sequence a *Haematococcus* act gene promoter, a *Haematococcus* Rubisco gene promoter, or a β-tubulin promoter.

9. The expression vector of claim 7, wherein said nucleic acid molecule which encodes a protein is a carotenoid biosynthesis gene, an astaxanthin biosynthesis gene, or an isoprenoid biosynthesis gene.

10. A method for transforming a eukaryotic cell comprising contacting said eukaryotic cell with the expression vector of claim 1 under conditions favoring transformation thereby.

11. The method of claim 10, wherein said eukaryotic cell is a single cell plant.

12. The method of claim 11, wherein said single cell plant is an algae.

13. The method of claim 12, wherein said algae is a *H. pluviales*.

14. A method for determining if a cell has been successfully transformed comprising contacting said cell with the expression vector of claim 1 and determining resistance to a herbicide as a determination of successful transformation.

15. The method of claim 10, comprising transforming said cell via particle bombardment.

16. The method of claim 15, comprising carrying out said particle bombardment with tungsten particles of from 0.4 to 1.7 μm in diameter, a pressure of from 500 to 2500 pounds per square inch, in vacuo.

17. A transgenic plant cell comprising the expression vector of claim 1 in its nuclear genome.

18. The transgenic plant cell of claim 17, comprising a plurality of copies of said expression vector in its genome.

* * * * *

SEQUENCE LISTING

```
<160> NUMBER OF SEQ ID NOS: 10

<210> SEQ ID NO 1
<211> LENGTH: 6149
<212> TYPE: DNA
<213> ORGANISM: H. pluvialis
<220> FEATURE:
<222> LOCATION: 4212
<223> OTHER INFORMATION: n at 4212 is unknown
```

-continued

```
<400> SEQUENCE: 1
atcggtgagg ggttcaagtg ccagctcagt caaacatcgt gcattcagga ggcacagtta      60
gaggcgtggt tgcagacgta ggtgagcagt tgggtgctgc tgctgctgtg atctgataca     120
tgttgaaaac tgagcggaat ggccatgtat tgttgtttga ttactcatgg ccatgcactg     180
agcatgcagc aagccatacc catccaggag ttgtcttcac ttcctttccc gcgcttgctt     240
gctttcatcc gctttctttc catatgctgt gttgtgatcc ctccctcccc tcctccctcc     300
ttaccctgcc ccaccctgg tggtgtgtgg ccaggtggct gtgacgcact gcctgctgag     360
cgctgacctg gtgagcatga gcgccaggct gggccgagct gcctgggtgg ccaccactcg     420
gctgtatgct gctcagcaag aggtggcagg ccaggcccat gtggcagcca tgcacctggt     480
ggcaatcggg gatagggctg cggcagaagc agtgtacagg tggcgcgggg caggagcagg     540
gacaggggct atagggtccc cggccaggtc taccctgact gctggggtta aggctagggc     600
tagggctagg gctagggcta gggctagggc tagggctagg gctagggcta gggctagggc     660
tagggctagg gctagggcta gggctagggc tagggctagg gctagggcta gggctaagga     720
caaggggtgg gggcgaaggg tggggtttg cagcagccag ggtcagccct gggccaacag     780
tagctactgc acatccccac aatctcctac aggcagcaca ggctaacgtg cgcggactgc     840
atcaccgggt acacagttga tgacatctta tcgaagcatc tcaccacacg acacatcaca     900
attagttgca agggttcctg tcggtgttga ggtttgagtt ggtctgtatg caggggcctg     960
atggaaaaac tgtagtagct gagtgagatt acccacagcc aagcatgttg ttccatgttg    1020
aacaggtttt gtttggtctg atggaaaaac tgttgaaatg cttcctgtca tcgttccgct    1080
gtacgccatt gtacgccgtt gactgatgga ctgattgttt gactgatgga agaactgtgt    1140
agacctcagc cccctcagca cattagcata tctcgacaca tcagccatgc gcacaccgag    1200
ttcgccttgt catgcgcagc caccctgtag aatgaagtca cgtaagtagt ggctgccgcg    1260
aggtcgcctt ggtattgtct ctggcttgat atagcgctga ctgacgggtg gtgacggtgc    1320
tcgtgcgcta tagatgccac tagaggcccg cccaccctcgc gcctgagccg caaaacccgg    1380
cggggtcgtc acgatgaggg catcttacct cgacgatgta ccgaccccgg gagctgtccc    1440
gctggactgg cggatcgcgg ctgcccaact tgggcactga gcgttggctg tggatcaaca    1500
tcattggcgc cgatgtcagc ctgggccagc aggtgcagcg gctgaccggc tatggaccgg    1560
ctatggaccg gctacgatag cggatgcagc gttcctccgc atgcagagat gcactggacc    1620
agtaccggag acggcgccag cgggatacac ggattagtgc gcctgaactg cggtgtgccc    1680
catgaatgac catgccagcc caaggggcg gcattgaagc ggccctagag agctagtggc    1740
aaggcagcac tagacaactt atgagctaag gtcagggagc tatgaggctg caagattagg    1800
ggcctgattt gagttgttca gtcgcacgtc ttcacgacgt tacggctgcc atcttaccca    1860
gtcggctaaa gcaggccacc accattggcg tcacgcgtga tcgtcttgaa atgacagcta    1920
gtccaaacac caggctcagc tcgtatggtt tggcgagggc gtttcgtcgg ttgaacgacg    1980 tgccttaat gaaaattcgt ggccatacct tcatcgcttg agccaaccat ccagcatcaa    2040
ctctgacaat gcagacagca atgcgtggcc aagccagcgg ttcaggatgc acttccagca    2100
ggcaagctcg cggtcattgg tcaaggcgct ctgtgcgtga gcgaggtgct ctcagggtgg    2160
ttgccaagga ctaccccacg ccggatttcc aatcatcgga cacataccag gaggccctgt    2220
ccctgtcgac caagctgcga aatacacccc ggcccgccaa gcctttgcgc gttgtcattg    2280
ctggggccgg cctggcaggc ctctcggctg caaaatacct ggcagatgca gggcaccacc    2340
```

-continued

```
cagttgtgct ggagggccgc gacgtgctag gcggcaaggt aaggacttgc gagtgtcgaa    2400
tgccacgccg gcccgttcca aacgcccaca agctgtccgg ccacctcaca aactcattgg    2460
cgcacaggtg gccgcgtgga aggacgagga cggtgattgg tacgagactg gccttcacat    2520
tttctttggt gcttacccca acatccagaa cctgttcaaa gagttgggca tccaagacag    2580
gtaggaggtg cacccagtag tgtcaacgca ttgcctagca agcgcctcag tcaacaagac    2640
caccatgagc actgttcttg atgtgggcat gtgcctgcct gcaggctgc agtggaagga     2700
gcattccatg atcttttgcca tgccagacgc ccctggggag ttttctcgct ttgacttccc   2760
tgagctgcct gcgccctgga acggcatcat cgccatcttg cggaacaacc agatgctcag   2820
ctggcctgag aagatccggt ttgccatcgg cctgctgcct gctatcatct ttgggcagcg   2880
ctactgtgaa gagcaggacg agctgaccgt gacagagtgg atgcgcaagc agggtgtgcc   2940
agaccgagtc aatgaggaag tgttcatcgc catggccaag gccttgaact tcatcaaccc   3000
tgacgaccta tccatgacag tggtgctcac agcactgaac cgcttcctgc aggcaagtgt   3060
tgggcctagg cagtcagggg tcaggggcct gcagggccag cttgcatctg cccgaccttc   3120
agggccgccg cctccctcac aaagcatgca ccctccacaa cccgcctgtc tgtctgccca   3180
acaccagctt atggtccaaa tccaccacaa ccgcctctca ccctcctgcc cctgctttca   3240
gcctgagcac tgcagtcctg tcaccagcaa atgtgtggcg gctgcacttc ttgtccctgc   3300
cgccaatcgc tttcagtgtg gcctggccag cttgtgacag tggctagagc tccaagctct   3360
gcaaagactg agacaagctg tggtttgcat tgcctgggct gcaggagcag catggcagca   3420
agatggcttt cttggatggc gccccacctg agcgcctctg tcagccaatg gtggactact   3480
tcaaggcacg aggcggcgac ctcatgttca actcccgggt caagcagatt gtgttgaatg   3540
tgaggtccct ggctctcagc ctcgccgcct cctgcagacg ctgcatgcca tgtgcagtat   3600
caccatgcca cacacgtcgg catcagctgc aggcctagct ctcgcgccgc agtcacagtt   3660
gaacccaaca catgtgcaag tcatcaccct gtgcagcagg caggggcagg ctgggtgcct   3720
gggcctgtca tccactgcag ccacagtctt gagtggaggg tacagtcatt aactctgccc   3780
atgaggtgtc agagtctttc atgggtgcta tatggtcgct cttggcgtgc aggacgacaa   3840
gagtgtcaag cacctggccc tcaccaatgg tcagacagtt gagggcgacc tctacatctc   3900
agccatgcca ggtgtgtgcc tatggtgcag ctgggctgtg tgcccctaag cagccacaca   3960
agcactggat gccatcaccc attgctgcat gacataggca caaggatgat agccaacgac   4020
atggatgagg cacctgggca cagaggcaca cgttgtggcc tgcacagcct gagtcatgaa   4080
ttgaggggggg agagccaggt aggctgtaat tgtggcactg acctccacaa aaccataaca   4140
caccagattg actgagtcca gttaggcttg ggggcttccc ttcagtttgt tcagaaccag   4200
gatgcttggc tnctccctac catgcgctga catgtgtgct tgcattgatg tggtctcgca   4260
gtggacatca tgaagatcct catgcctgac ccctgggcct ccatgcccta cttcaagcag   4320
ctgaacggcc tggaggggggt gcctgtgatc aacatccaca tctggttcga tcgcaagctg   4380
actacggtgg accacctgtt gttcagtcgg tcaccgctgc tgtctgtgta cgctgacatg   4440
agcaccacgt gcaaggagta tgctgacgac aagaagagca tgcttgagct ggtgtttgcg   4500
ccggccaagg agtggattgg ccggcctgac gaggagatca tcgcagccac catgacagag   4560
ctggagcggc tgttcccgac agaggtcagg gctgaccagt ccatggccaa ggtaggcggg   4620
tcaggcacca gccagcactg ccaggcctgc aggttaagag gcttgtgagg ggtgcagctc   4680
tgggcagata gcagctacag ccagctaacg gtgccggggt tgtgagtgaa tggcgcccac   4740
```

```
tgcctgaagc accaccctgc tcagcttgct ctgctgtgcc agcattggct gcctgctgtc    4800
gaagtacttg tggtgatggg tgatggtggc atgatgtgca gatcttgaag tacaaggtgg    4860
tgaagactcc attgtctgtg tacaagtcca ctgctgggcg ggagaagttc aggtgagcct    4920
cgcgacagcc gacagtggaa tgcactgcag cccttgtggc tgcctgactg gctttcttgt    4980
cagccgctct ctcgtgacca taactgatgc tgccgtacct tatctgctgc tgctgctgtc    5040
atgctggtgc taatggtggt gccccggtgc tgctgctgct gtgctgcaga cccactcagc    5100
gctccccaat ctccaacttc taccttgcgg gtgattacac caagcagaag tacctgctcc    5160
atggagggtg cagtgttctc cggcaagctg gtcaccgaag ccattgtaga ggactggagc    5220
gctcggggtg tgaccagcag cgctgccagc cgccagcctg ccctggctgc agccggtgtg    5280
gtggcagggt cggctgcagt gattggggcg gcgttggttg cagccagtgg tgcaatagcc    5340
ggtgggatgt aagtgatgaa agaatggcac ctggtagatg aggcagcatt tatagaaatg    5400
gcagcaccct cgctgcctaa tgcttgtggt gtatactatt gacctcggga gttgaggccc    5460
gcagccattg tgtggctatc gcatggggtg gtgcatcgct gctcaatgcc gacaacattg    5520
ggatggccta gaacttattg ctaggtagtg tgacctggac aagagattgg gtatgggtct    5580
ggtgaggaag ggcaggcact atgggcgagc attctgagag gttgggcagg cgtgctgtag    5640
tcctgcgatg agttggagtg tctaaacggc agtaacggat atggggtcac acggtttaca    5700
cgaacattgc tgaaatcgag gatcatcacg aagcgtgcaa gaaacgtcat gcaacatgca    5760
aacaagccaa aattcaaacg atggcgaacg tggcgagaaa ggaagggaag aaagcgaaag    5820
gagcgggcgc tagggcgctg gcaagtgtag cggtcacgct gcgcgtaacc accacacccg    5880
ccgcgcttaa tgcgccgcta cagggcgcgt cccattcgcc attcaggctg cgcaactgtt    5940
gggaagggcg atcggtgcgg gcctcttcgc tattacgcca gctggcgaaa ggggatgtg     6000 ctgcaaggcg attaagttgg gtaacgccag ggttttccca gtcacgacgt tgtaaaacga    6060
cggccagtga attgtaatac gactcactat agggcgaatt gggtaccggg ccccccctcg    6120
aggtcgacgg tatcgataag cttgatatc                                       6149
```

<210> SEQ ID NO 2
<211> LENGTH: 570
<212> TYPE: PRT
<213> ORGANISM: H. pluvialis

<400> SEQUENCE: 2

```
Met Gln Thr Thr Met Arg Gly Gln Ala Ser Gly Ser Gly Cys Thr Ser
1               5                   10                  15

Gly Arg Gln Ala Arg Gly His Trp Ser Arg Arg Ser Val Arg Glu Arg
            20                  25                  30

Gly Ala Leu Arg Val Val Ala Lys Asp Tyr Pro Thr Pro Asp Phe Gln
        35                  40                  45

Ser Ser Asp Thr Tyr Gln Glu Ala Leu Ser Leu Ser Thr Lys Leu Arg
    50                  55                  60

Asn Ala Pro Arg Pro Ala Lys Pro Leu Arg Val Ile Ala Gly Ala
65                  70                  75                  80

Gly Leu Ala Gly Leu Ser Ala Ala Lys Tyr Leu Ala Asp Ala Gly His
                85                  90                  95

His Pro Val Val Leu Glu Gly Arg Asp Val Leu Gly Gly Lys Val Ala
            100                 105                 110

Ala Trp Lys Asp Glu Asp Gly Asp Trp Tyr Glu Thr Gly Leu His Ile
        115                 120                 125
```

Phe Phe Gly Ala Tyr Pro Asn Ile Gln Asn Leu Phe Lys Glu Leu Gly
    130                 135                 140

Ile Gln Asp Arg Leu Gln Trp Lys Glu His Ser Met Ile Phe Ala Met
145                 150                 155                 160

Pro Asp Ala Pro Gly Glu Phe Ser Arg Phe Asp Phe Pro Glu Leu Pro
                    165                 170                 175

Ala Pro Trp Asn Gly Ile Ile Ala Ile Leu Arg Asn Asn Gln Met Leu
                180                 185                 190

Ser Trp Pro Glu Lys Ile Arg Phe Arg Ile Gly Leu Leu Pro Ala Ile
            195                 200                 205

Ile Phe Gly Gln Arg Tyr Cys Glu Glu Gln Asp Glu Leu Thr Val Thr
    210                 215                 220

Glu Trp Met Arg Lys Gln Gly Val Pro Asp Arg Val Asn Glu Glu Val
225                 230                 235                 240

Phe Ile Ala Met Ala Lys Ala Leu Asn Phe Ile Asn Pro Asp Asp Leu
                    245                 250                 255

Ser Met Thr Val Val Leu Thr Ala Leu Asn Arg Phe Leu Gln Glu Gln
                260                 265                 270

His Gly Ser Lys Met Ala Phe Leu Asp Gly Ala Pro Pro Glu Arg Leu
            275                 280                 285

Cys Gln Pro Met Val Asp Tyr Phe Lys Ala Arg Gly Gly Asp Leu Met
    290                 295                 300

Phe Asn Ser Arg Val Lys Gln Ile Val Leu Asn Asp Asp Lys Ser Val
305                 310                 315                 320

Lys His Leu Ala Leu Thr Asn Gly Gln Thr Val Glu Gly Asp Leu Tyr
                    325                 330                 335

Ile Ser Ala Met Pro Val Asp Ile Met Lys Ile Leu Met Pro Asp Pro
                340                 345                 350

Trp Ala Ser Met Pro Tyr Phe Lys Gln Leu Asn Gly Leu Glu Gly Val
            355                 360                 365

Pro Val Ile Asn Ile His Ile Trp Phe Asp Arg Lys Leu Thr Thr Val
    370                 375                 380

Asp His Leu Leu Phe Ser Arg Ser Pro Leu Leu Ser Val Tyr Ala Asp
385                 390                 395                 400

Met Ser Thr Thr Ser Lys Glu Tyr Arg Asp Lys Lys Ser Met Leu
                    405                 410                 415

Glu Leu Val Phe Ala Pro Ala Lys Glu Trp Ile Gly Arg Pro Asp Glu
            420                 425                 430

Glu Ile Ile Ala Ala Thr Met Thr Glu Leu Glu Arg Leu Phe Pro Thr
    435                 440                 445

Glu Val Arg Ala Asp Gln Ser Met Ala Lys Ile Leu Lys Tyr Lys Val
    450                 455                 460

Val Lys Thr Pro Leu Ser Val Tyr Lys Ser Thr Ala Gly Arg Glu Lys
465                 470                 475                 480

Phe Arg Pro Thr Gln Arg Ser Pro Ile Ser Asn Phe Tyr Leu Ala Gly
                    485                 490                 495

Asp Tyr Thr Lys Gln Lys Tyr Leu Ala Ser Met Glu Gly Ala Val Phe
                500                 505                 510

Ser Gly Lys Leu Val Thr Glu Ala Ile Val Glu Asp Trp Ser Ala Arg
            515                 520                 525

Gly Val Thr Ser Ser Ala Ala Ser Arg Gln Pro Ala Leu Ala Ala Ala
    530                 535                 540

Gly Val Val Gly Arg Val Gly Ser Ser Asp Trp Ala Arg Trp Leu Gln

```
                545                 550                 555                 560
            Pro Val Gly Ala Ile Ala Gly Gly Cys Lys
                            565                 570

<210> SEQ ID NO 3
<211> LENGTH: 569
<212> TYPE: PRT
<213> ORGANISM: H. pluvialis

<400> SEQUENCE: 3

Met Gln Thr Thr Met Arg Gly Gln Ala Ser Gly Ser Gly Cys Thr Ser
1               5                   10                  15

Gly Arg Gln Ala Arg Gly His Trp Ser Arg Arg Ser Val Arg Glu Arg
            20                  25                  30

Gly Ala Leu Arg Val Val Ala Lys Asp Tyr Pro Thr Pro Asp Phe Gln
        35                  40                  45

Ser Ser Asp Thr Tyr Gln Glu Ala Leu Ser Leu Ser Thr Lys Leu Arg
50                  55                  60

Asn Ala Pro Arg Pro Ala Lys Pro Leu Arg Val Val Ile Ala Gly Ala
65                  70                  75                  80

Gly Leu Ala Gly Leu Ser Ala Ala Lys Tyr Leu Ala Asp Ala Gly His
            85                  90                  95

His Pro Val Val Leu Glu Gly Arg Asp Val Leu Gly Gly Lys Val Ala
        100                 105                 110

Ala Trp Lys Asp Glu Asp Gly Asp Trp Tyr Glu Thr Gly Leu His Ile
    115                 120                 125

Phe Phe Gly Ala Tyr Pro Asn Ile Gln Asn Leu Phe Lys Glu Leu Gly
130                 135                 140

Ile Gln Asp Arg Leu Gln Trp Lys Glu His Ser Met Ile Phe Ala Met
145                 150                 155                 160

Pro Asp Ala Pro Gly Glu Phe Ser Arg Phe Asp Phe Pro Glu Leu Pro
            165                 170                 175

Ala Pro Trp Asn Gly Ile Ile Ala Ile Leu Arg Asn Asn Gln Met Leu
        180                 185                 190

Ser Trp Pro Glu Lys Ile Arg Phe Arg Ile Gly Leu Leu Pro Ala Ile
    195                 200                 205

Ile Phe Gly Gln Arg Tyr Cys Glu Glu Gln Asp Glu Leu Thr Val Thr
210                 215                 220

Glu Trp Met Arg Lys Gln Gly Val Pro Asp Arg Val Asn Glu Val
225                 230                 235                 240

Phe Ile Ala Met Ala Lys Ala Leu Asn Phe Ile Asn Pro Asp Asp Leu
            245                 250                 255

Ser Met Thr Val Val Leu Thr Ala Leu Asn Arg Phe Leu Gln Glu Gln
        260                 265                 270

His Gly Ser Lys Met Ala Phe Leu Asp Gly Ala Pro Pro Glu Arg Leu
    275                 280                 285

Cys Gln Pro Met Val Asp Tyr Phe Lys Ala Arg Gly Gly Asp Leu Met
290                 295                 300

Phe Asn Ser Arg Val Lys Gln Ile Val Leu Asn Asp Asp Lys Ser Val
305                 310                 315                 320

Lys His Leu Ala Leu Thr Asn Gly Gln Thr Val Glu Gly Asp Leu Tyr
            325                 330                 335

Ile Ser Ala Met Pro Val Asp Ile Met Lys Ile Leu Pro Asp Pro
        340                 345                 350

Trp Ala Ser Met Pro Tyr Phe Lys Gln Leu Asn Gly Leu Glu Gly Val
```

|     |     |     |     |     |     |     |     |     |     |
| --- | --- | --- | --- | --- | --- | --- | --- | --- | --- |
|     |     | 355 |     |     | 360 |     |     | 365 |     |
| Pro | Val | Ile | Asn | Ile | His | Ile | Trp | Phe | Asp | Arg | Lys | Leu | Thr | Thr | Val |
| 370 |     |     |     | 375 |     |     |     | 380 |     |
| Asp | His | Leu | Leu | Phe | Ser | Arg | Ser | Pro | Leu | Leu | Ser | Val | Tyr | Ala | Asp |
| 385 |     |     |     | 390 |     |     |     | 395 |     |     |     | 400 |
| Met | Ser | Thr | Thr | Ser | Lys | Glu | Tyr | Arg | Asp | Asp | Lys | Lys | Ser | Met | Leu |
|     |     |     |     | 405 |     |     |     | 410 |     |     |     | 415 |
| Glu | Leu | Val | Phe | Ala | Pro | Ala | Lys | Glu | Trp | Ile | Gly | Arg | Pro | Asp | Glu |
|     |     |     | 420 |     |     |     | 425 |     |     |     | 430 |
| Glu | Ile | Ile | Ala | Ala | Thr | Met | Thr | Leu | Glu | Arg | Leu | Phe | Pro | Thr |
|     |     |     | 435 |     |     |     | 440 |     |     |     | 445 |
| Glu | Val | Arg | Ala | Asp | Gln | Ser | Met | Ala | Lys | Ile | Leu | Lys | Tyr | Lys | Val |
|     | 450 |     |     |     | 455 |     |     |     | 460 |
| Val | Lys | Thr | Pro | Leu | Ser | Val | Tyr | Lys | Ser | Thr | Ala | Gly | Arg | Glu | Lys |
| 465 |     |     |     | 470 |     |     |     | 475 |     |     |     | 480 |
| Phe | Arg | Pro | Thr | Gln | Arg | Ser | Pro | Ile | Ser | Asn | Phe | Tyr | Leu | Ala | Gly |
|     |     |     | 485 |     |     |     | 490 |     |     |     | 495 |
| Asp | Tyr | Thr | Lys | Gln | Lys | Tyr | Arg | Ala | Ser | Met | Glu | Gly | Ala | Val | Phe |
|     |     | 500 |     |     |     | 505 |     |     |     | 510 |
| Ser | Gly | Lys | Leu | Val | Thr | Glu | Ala | Ile | Val | Glu | Asp | Trp | Ser | Ala | Arg |
|     | 515 |     |     |     | 520 |     |     |     | 525 |
| Gly | Val | Thr | Ser | Ser | Ala | Ala | Ser | Arg | Gln | Pro | Ala | Leu | Ala | Ala | Ala |
|     | 530 |     |     |     | 535 |     |     |     | 540 |
| Gly | Val | Val | Gly | Arg | Val | Gly | Ser | Ser | Asp | Trp | Ala | Arg | Trp | Leu | Gln |
| 545 |     |     |     | 550 |     |     |     | 555 |     |     |     | 560 |
| Pro | Val | Gly | Ala | Ile | Ala | Gly | Gly | Cys |
|     |     |     |     | 565 |

<210> SEQ ID NO 4
<211> LENGTH: 226
<212> TYPE: DNA
<213> ORGANISM: Artificial sequence
<220> FEATURE:
<223> OTHER INFORMATION: Nucleotide sequence from vector pdsMOD4.1

<400> SEQUENCE: 4

```
ttgtaaaacg acggccagtg aattgtaata cgactcacta tagggcgaat tgggtaccgg      60
gcccccccte gaggtcgacg gtatcgataa gcttgatatc gaattcctgc agcccggggg     120
atccactagt tctagagcgg ccgccaccgc ggtggagctc cagcttttgt tccctttagt     180
gagggttaat ttcgagcttg gcgtaatcat ggtcatagct gtttcc                    226
```

<210> SEQ ID NO 5
<211> LENGTH: 8742
<212> TYPE: DNA
<213> ORGANISM: Artificial sequence
<220> FEATURE:
<223> OTHER INFORMATION: Vector containing the artificial sequence
         SEQ ID NO: 4
<220> FEATURE:
<222> LOCATION: 4545
<223> OTHER INFORMATION: n at 4545 is unknown

<400> SEQUENCE: 5

```
cacctaaatt gtaagcgtta atattttgtt aaaattcgcg ttaaattttt gttaaatcag      60
ctcatttttt aaccaatagg ccgaaatcgg caaaatccct tataaatcaa agaatagac     120
cgagataggg ttgagtgttg ttccagtttg gaacaagagt ccactattaa agaacgtgga    180
ctccaacgtc aaagggcgaa aaaccgtcta tcagggcgat ggcccactac gtgaaccatc    240
```

```
accctaatca agttttttgg ggtcgaggtg ccgtaaagca ctaaatcgga accctaaagg    300
gagcccccga tttagagctt gacggggaaa gccatcggtg aggggttcaa gtgccagctc    360
agtcaaacat cgtgcattca ggaggcacag ttagaggcgt ggttgcagac gtaggtgagc    420
agttgggtgc tgctgctgct gtgatctgat acatgttgaa aactgagcgg aatggccatg    480
tattgttgtt tgattactca tggccatgca ctgagcatgc agcaagccat acccatccag    540
gagttgtctt cacttccttt cccgcgcttg cttgctttca tccgctttct ttccatatgc    600
tgtgttgtga tccctccctc ccctcctccc tccttaccct gccccacccc tggtggtgtg    660
tggccaggtg gctgtgacgc actgcctgct gagcgctgac ctggtgagca tgagcgccag    720
gctgggccga gctgcctggg tggccaccac tcggctgtat gctgctcagc aagaggtggc    780
aggccaggcc catgtggcag ccatgcacct ggtggcaatc ggggatagg ctgcggcaga    840 agcagtgtac aggtgggcgc gggcaggagc agggacaggg gctataggt cccggccag    900 gtctaccctg actgctgggg ttaaggctag ggctagggct agggctaggg ctagggctag    960
ggctagggct agggctaggg ctagggctag ggctagggct agggctaggg ctagggctag   1020
ggctagggct agggctaggg ctagggctaa ggacaagggg tgggggcgaa gggtgggggt   1080
ttgcagcagc cagggtcagc cctgggccaa cagtagctac tgcacatccc cacaatctcc   1140
tacaggcagc acaggctaac gtgcgcggac tgcatcaccg ggtacacagt tgatgacatc   1200
ttatcgaagc atctcaccac acgacacatc acaattagtt gcaagggttc ctgtcggtgt   1260
tgaggtttga gttggtctgt atgcaggggc ctgatgaaaa aactgtagta gctgagtgag   1320
attacccaca gccaagcatg ttgttccatg ttgaacaggt tttgtttggt ctgatggaaa   1380
aactgttgaa atgcttcctg tcatcgttcc gctgtacgcc attgtacgcc gttgactgat   1440
ggactgattg tttgactgat ggaagaactg tgtagacctc agcccctca gcacattagc   1500 atatctcgac acatcagcca tgcgcacacc gagttcgcct tgtcatgcgc agccaccctg   1560
tagaatgaag tcacgtaagt agtggctgcc gcgaggtcgc cttggtattg tctctggctt   1620
gatatagcgc tgactgacgg gtggtgacgg tgctcgtgcg ctatagatgc cactagaggc   1680
ccgcccacct cgcgcctgag ccgcaaaacc cggcggggtc gtcacgatga gggcatctta   1740
cctcgacgat gtaccgaccc cgggagctgt cccgctggac tggcggatcg cggctgccca   1800
acttgggcac tgagcgttgg ctgtggatca acatcattgg cgccgatgtc agcctgggcc   1860
agcaggtgca gcggctgacc ggctatggac cggctatgga ccggctacga tagcggatgc   1920
agcgttcctc cgcatgcaga gatgcactgg accagtaccg gagacggcgc cagcgggata   1980
cacggattag tgcgcctgaa ctgcggtgtg ccccatgaat gaccatgcca gccccaaggg   2040
gcggcattga agcggcccta gagagctagt ggcaaggcag cactagacaa cttatgagct   2100
aaggtcaggg agctatgagg ctgcaagatt aggggcctga tttgagttgt tcagtcgcac   2160
gtcttcacga cgttacggct gccatcttac ccagtcggct aaagcaggcc accaccattg   2220
gcgtcacgcg tgatcgtctt gaaatgacag ctagtccaaa caccaggctc agctcgtatg   2280
gtttggcgag ggcgtttcgt cggttgaacg acgtgccttt aatgaaaatt cgtggccata   2340
ccttcatcgc ttgagccaac catccagcat caactctgac aatgcagaca gcaatgcgtg   2400
gccaagccac cggttcagga tgcacttcca gcaggcaagc tcgcggtcat tggtcaaggc   2460
gctctgtgcg tgagcgaggt gctctcaggg tggttgccaa ggactacccc acgccggatt   2520
tccaatcatc ggacacatac caggaggccc tgtccctgtc gaccaagctg cgaaatacac   2580
cccggcccgc caagcctttg cgcgttgtca ttgctggggc cggcctggca ggcctctcgg   2640
```

```
ctgcaaaata cctggcagat gcagggcacc acccagttgt gctggagggc cgcgacgtgc    2700
taggcggcaa ggtaaggact tgcgagtgtc gaatgccacg ccggcccgtt ccaaacgccc    2760
acaagctgtc cggccacctc acaaactcat tggcgcacag gtggccgcgt ggaaggacga    2820
ggacggtgat tggtacgaga ctggccttca cattttcttt ggtgcttacc ccaacatcca    2880
gaacctgttc aaagagttgg gcatccaaga caggtaggag gtgcacccag tagtgtcaac    2940
gcattgccta gcaagcgcct cagtcaacaa gaccaccatg agcactgttc ttgatgtggg    3000
catgtgcctg ccttgcaggc tgcagtggaa ggagcattcc atgatctttg ccatgccaga    3060
cgcccctggg gagttttctc gctttgactt ccctgagctg cctgcgccct ggaacggcat    3120
catcgccatc ttgcggaaca accagatgct cagctggcct gagaagatcc ggtttgccat    3180
cggcctgctg cctgctatca tctttgggca gcgctactgt gaagagcagg acgagctgac    3240
cgtgacagag tggatgcgca agcagggtgt gccagaccga gtcaatgagg aagtgttcat    3300
cgccatggcc aaggccttga acttcatcaa ccctgacgac ctatccatga cagtggtgct    3360
cacagcactg aaccgcttcc tgcaggcaag tgttgggcct aggcagtcag gggtcagggg    3420
cctgcagggc cagcttgcat ctgcccgacc ttcagggccg ccgcctccct cacaaagcat    3480
gcaccctcca caaccgcct gtctgtctgc ccaacaccag cttatggtcc aaatccacca    3540
caaccgcctc tcaccctcct gcccctgctt tcagcctgag cactgcagtc ctgtcaccag    3600
caaatgtgtg gcggctgcac ttcttgtccc tgccgccaat cgctttcagt gtggcctggc    3660
cagcttgtga cagtggctag agctccaagc tctgcaaaga ctgagacaag ctgtggtttg    3720
cattgcctgg gctgcaggag cagcatggca gcaagatggc tttcttggat ggcgcccac    3780 ctgagcgcct ctgtcagcca atggtggact acttcaaggc acgaggcggc gacctcatgt    3840
tcaactcccg ggtcaagcag attgtgttga atgtgaggtc cctggctctc agcctcgccg    3900
cctcctgcag acgctgcatg ccatgtgcag tatcaccatg ccacacacgt cggcatcagc    3960
tgcaggccta gctctcgcgc cgcagtcaca gttgaaccca acacatgtgc aagtcatcac    4020
cctgtgcagc aggcagggc aggctggtg cctgggcctg tcatccactg cagccacagt    4080
cttgagtgga gggtacagtc attaactctg cccatgaggt gtcagagtct ttcatgggtg    4140
ctatatggtc gctcttggcg tgcaggacga caagagtgtc aagcacctgg ccctcaccaa    4200
tggtcagaca gttgagggcg acctctacat ctcagccatg ccaggtgtgt gcctatggtg    4260
cagctgggct gtgtgcccct aagcagccac acaagcactg gatgccatca cccattgctg    4320
catgacatag gcacaaggat gatagccaac gacatggatg aggcacctgg gcacagaggc    4380
acacgttgtg gcctgcacag cctgagtcat gaattgaggg gggagagcca ggtaggctgt    4440
aattgtggca ctgacctcca caaaaccata acacaccaga ttgactgagt ccagttaggc    4500 ttggggctt cccttcagtt tgttcagaac caggatgctt ggctnctccc taccatgcgc    4560
tgacatgtgt gcttgcattg atgtggtctc gcagtggaca tcatgaagat cctcatgcct    4620
gaccctgggg cctccatgcc ctacttcaag cagctgaacg gcctggaggg ggtgcctgtg    4680
atcaacatcc acatctggtt cgatcgcaag ctgactacgg tggaccacct gttgttcagt    4740
cggtcaccgc tgctgtctgt gtacgctgac atgagcacca cgtgcaagga gtatgctgac    4800
gacaagaaga gcatgcttga gctggtgttt gcgccggcca aggagtggat tggcggcct    4860 gacgaggaga tcatcgcagc caccatgaca gagctggagc ggctgttccc gacagaggtc    4920
agggctgacc agtccatggc caaggtaggc gggtcaggca ccagccagca ctgccaggcc    4980
tgcaggttaa gaggcttgtg aggggtgcag ctctgggcag atagcagcta cagccagcta    5040
```

```
acggtgccgg ggttgtgagt gaatggcgcc cactgcctga agcaccaccc tgctcagctt   5100
gctctgctgt gccagcattg gctgcctgct gtcgaagtac ttgtggtgat gggtgatggt   5160
ggcatgatgt gcagatcttg aagtacaagg tggtgaagac tccattgtct gtgtacaagt   5220
ccactgctgg gcgggagaag ttcaggtgag cctcgcgaca gccgacagtg gaatgcactg   5280
cagcccttgt ggctgcctga ctggcttcct tgtcagccgc tctctcgtga ccataactga   5340
tgctgccgta ccttatctgc tgctgctgct gtcatgctgg tgctaatggt ggtgccccgg   5400
tgctgctgct gctgtgctgc agacccactc agcgctcccc aatctccaac ttctaccttg   5460
cgggtgatta caccaagcag aagtaccgcg cctccatgga gggtgcagtg ttctccggca   5520
agctggtcac cgaagccatt gtagaggact ggagcgctcg gggtgtgacc agcagcgctg   5580
ccagccgcca gcctgccctg gctgcagccg gtgtggtggc agggtcggct gcagtgattg   5640
gggcggcgtt ggttgcagcc agtggtgcaa tagccggtgg gatgtaagtg atgaaagaat   5700
ggcacctggt agatgaggca gcatttatag aaatggcagc accctcgctg cctaatgctt   5760
gtggtgtata ctattgacct cgggagttga ggcccgcagc cattgtgtgg ctatcgcatg   5820
gggtggtgca tcgctgctca atgccgacaa cattgggatg cctagaact tattgctagg    5880 tagtgtgacc tggacaagag attgggtatg gtctggtga ggaagggcag gcactatggg    5940
cgagcattct gagaggttgg gcaggcgtgc tgtagtcctg cgatgagttg gagtgtctaa   6000
acggcagtaa cggatatggg gtcacacggt ttacacgaac attgctgaaa tcgaggatca   6060
tcacgaagcg tgcaagaaac gtcatgcaac atgcaaacaa gccaaaattc aaacgatggc   6120
gaacgtggcg agaaaggaag ggaagaaagc gaaaggagcg ggcgctaggg cgctggcaag   6180
tgtagcggtc acgctgcgcg taaccaccac acccgccgcg cttaatgcgc cgctacaggg   6240
cgcgtcccat tcgccattca ggctgcgcaa ctgttgggaa gggcgatcgg tgcgggcctc   6300
ttcgctatta cgccactgg cgaaagggg atgtgctgca aggcgattaa gttgggtaac    6360
gccagggttt tcccagtcac gacgttgtaa aacgacggcc agtgaattgt aatacgactc   6420
actatagggc gaattgggta ccgggccccc cctcgaggtc gacggtatcg ataagcttga   6480
tatcgaattc ctgcagcccg gggatccac tagttctaga gcggccgcca ccgcggtgga   6540
gctccagctt ttgttccctt tagtgagggt taatttcgag cttggcgtaa tcatggtcat   6600
agctgtttcc tgtgtgaaat tgttatccgc tcacaattcc acacaacata cgagccggaa   6660
gcataaagtg taaagcctgg ggtgcctaat gagtgagcta actcacatta attgcgttgc   6720
gctcactgcc cgctttccag tcgggaaacc tgtcgtgcca gctgcattaa tgaatcggcc   6780
aacgcgcggg gagaggcggt ttgcgtattg ggcgctcttc cgcttcctcg ctcactgact   6840
cgctgcgctc ggtcgttcgg ctgcggcgag cggtatcagc tcactcaaag gcggtaatac   6900
ggttatccac agaatcaggg gataacgcag gaaagaacat gtgagcaaaa ggccagcaaa   6960
aggccaggaa ccgtaaaaag gccgcgttgc tggcgttttt ccataggctc cgcccccctg   7020
acgagcatca caaaaatcga cgctcaagtc agaggtggcg aaacccgaca ggactataaa   7080
gataccaggc gtttccccct ggaagctccc tcgtgcgctc tcctgttccg accctgccgc   7140
ttaccggata cctgtccgcc tttctccctt cgggaagcgt ggcgctttct catagctcac   7200
gctgtaggta tctcagttcg gtgtaggtcg ttcgctccaa gctgggctgt gtgcacgaac   7260
cccccgttca gcccgaccgc tgcgccttat ccggtaacta tcgtcttgag tccaacccgg   7320
taagacacga cttatcgcca ctggcagcag ccactggtaa caggattagc agagcgaggt   7380
atgtaggcgg tgctacagag ttcttgaagt ggtggcctaa ctacggctac actagaagga   7440
```

```
cagtatttgg tatctgcgct ctgctgaagc cagttacctt cggaaaaaga gttggtagct    7500
cttgatccgg caaacaaacc accgctggta gcggtggttt ttttgtttgc aagcagcaga    7560
ttacgcgcag aaaaaaagga tctcaagaag atcctttgat cttttctacg ggtctgacg    7620 ctcagtggaa cgaaaactca cgttaaggga ttttggtcat gagattatca aaaaggatct    7680
tcacctagat ccttttaaat taaaaatgaa gttttaaatc aatctaaagt atatatgagt    7740
aaacttggtc tgacagttac caatgcttaa tcagtgaggc acctatctca gcgatctgtc    7800
tatttcgttc atccatagtt gcctgactcc ccgtcgtgta gataactacg atacgggagg    7860
gcttaccatc tggccccagt gctgcaatga taccgcgaga cccacgctca ccggctccag    7920
atttatcagc aataaaccag ccagccggaa gggccgagcg cagaagtggt cctgcaactt    7980
tatccgcctc catccagtct attaattgtt gccgggaagc tagagtaagt agttcgccag    8040
ttaatagttt gcgcaacgtt gttgccattg ctacaggcat cgtggtgtca cgctcgtcgt    8100
ttggtatggc ttcattcagc tccggttccc aacgatcaag gcgagttaca tgatccccca    8160
tgttgtgcaa aaaagcggtt agctccttcg gtcctccgat cgttgtcaga agtaagttgg    8220
ccgcagtgtt atcactcatg gttatggcag cactgcataa ttctcttact gtcatgccat    8280
ccgtaagatg cttttctgtg actggtgagt actcaaccaa gtcattctga gaatagtgta    8340
tgcggcgacc gagttgctct tgcccggcgt caatacggga taataccgcg ccacatagca    8400
gaactttaaa agtgctcatc attggaaaac gttcttcggg gcgaaaactc tcaaggatct    8460
taccgctgtt gagatccagt tcgatgtaac ccactcgtgc acccaactga tcttcagcat    8520
cttttacttt caccagcgtt tctgggtgag caaaaacagg aaggcaaaat gccgcaaaaa    8580
agggaataag ggcgacacgg aaatgttgaa tactcatact cttcctttt caatattatt    8640 gaagcattta tcagggttat tgtctcatga gcggatacat atttgaatgt atttagaaaa    8700
ataaacaaat aggggttccg cgcacatttc cccgaaaagt gc                       8742

<210> SEQ ID NO 6
<211> LENGTH: 2187
<212> TYPE: DNA
<213> ORGANISM: Artificial sequence
<220> FEATURE:
<223> OTHER INFORMATION: Actin-Promotor SmaI-Fragment

<400> SEQUENCE: 6
cccccgggca ggcagcggtg gggccagcag tggggcccaa tggcagcgcc tggggcctgg      60 aggggtagc ttaggcgggg cggcgggggg gggcggggtg ggaggcggtg tgggcgccca     120
ggcgttggct ctgctgcgtg ggggctgggc taggattggg tcaggccccc ctatgctgcc     180
gccccccgcc ccaggccccg ctgggtctga gggccctgcc ccccgcgcat ctccctgggt     240
gcggcagctg cagcggggca gccacgcccg cagccactcc tcgccagtgg acctgaccag     300
cccgcagctc acccaggcgc tgctggacga gtggcatggg ggggaggagc cagggggggg     360
ccctggtctg gccctagcc acaacagctt tgacttgagg ctcagggccg gccaataatg      420
gggtggttgg gaagggtagg ggggtccggg agggggktkg gkaagggtaa ggtagggtta     480
ggtaaggtag gctaggctca gggtgttatg catggcaatg gtagcaggcg tagctgcagc     540
tggggaagat tcatggtaaa cgtataaagg accagctg atggtgggcg aatgacggac       600
acctgcatgt attctttaca tttcaagtat ttcaaagttg gtttgcaacg atgtggggct     660
aggctatgca ataagactgc tacatgaggc cgggctgatc accgctcgtg acgtatggac     720
gtatctgacg tgatcaacct gaccccttacc gaaccctgac ctgcagtgcc caatccatga    780
```

```
tatcagctgg tgctctgtgc cacactattg cagtttacag cgatggatgc ttacttggct      840
tgcgttgctt ggattctgcg accgtggcct tccaatgcgg ttcacctttc aagccacgat      900
caatatcaca agcatgggtt gcatgagcgc taaccacctg cctttggaga cttgcgcgcc      960
atacccattg tgtgggatac agcaccccct ccacacaccc gagatcccca cggtcagctg     1020
tcgcgcttaa cccgctcccc cctcgcgcct cttgctcgtg atcattgtgg gttgccgcga     1080
cgtcaccgct ccgtcaacgt gctttcaaac agggatcaaa aatgctccat cacccggtgc     1140
agagtctttg ctgcaagcag cacaatggct gaggagggag aggtatctgc ccttgtctgc     1200
gacaatggct cggggatggt gaaagccggg ttcgctgggg atgatgcgcc ccgtgcagtc     1260
ttccccagca ttgtgggcag gccgcgccac acaggcgtga tggtgggcat ggggcaaaag     1320
gtaagaacgc tgtgtgcgac gaactgcatc gctgcagctg gcccagctca acgtggcgct     1380
ctatgtgtgc aggactcata cgtcggcgat gaggcacagt ccaagcgagg catcctgacg     1440
ctacgctacc caatcgagca cggcattgtc acaaactggg atgacatgga aaaaatttgg     1500
catcacacat ggttcaacga gcttcgcggt aaaaaatttg gcatcacaca tggttcaacg     1560
agcttcgcgt ggctccagag gtgagtagcg agtccctgag gtgcagcact ggctgccctg     1620
tttgcctctg ctttagccac tgattccctg gtcagtccca ggccaggact gacatgcatc     1680
tacatgcgtt gaagtgcaat gtcgcaagcc cagctcagcc acctatattg ggtgcagggc     1740
gcgtgggttt gccttccttc cctgtaatc tgtttccccg atgtacaaaa cgatagtgtg      1800
gtaggcctac aaggaaatgg tgtcatgggg gtccactgtc acgcctgagc tgatgctggt     1860
cacaaggctc gcagcacgcc aaagctcagc agggtggctc aggccatatg gctcaagtac     1920
gctgtgcctc caagctgggg ccatgtcact gcatggcgcc tgcatgtgtt aggaaacaaa     1980
cgctaggatg ggcgtgaggc cccttttcctg cccccttccc gcagctctag cagcagagcc     2040
atgagttagg gctagggtta gtcatggggc tgccttgcta gcttcgaatg ccggctgagc     2100
acattctagt tgcatgcatt ggatatgcac ttgcgtgcag cttcccgctc cccatccaga     2160
catttgttgt ccagctcccc gcccggg                                         2187
```

<210> SEQ ID NO 7
<211> LENGTH: 1300
<212> TYPE: DNA
<213> ORGANISM: Artificial sequence
<220> FEATURE:
<223> OTHER INFORMATION: rbsc-Promotor PstI-Fragment

<400> SEQUENCE: 7

```
ctgcagggcc agccactaat gctgcaacgg gaccagtaaa aggaacaggt tcaggaccag       60
caggtgtcga gtatcgcgcc agctttgtgt gtttccgtgc gtgtgtgttg gggcgctgtt      120
acatgccatg ccatgccacg tcactgcgac gacttctgat tgcagcggca agagcccggg      180
cagtcgctat ttgcagaaac gagaggtttt atctcttgag catggggtg accattggtg       240 aaacactcga ggacgatctc atgcattcaa tggatcttat tcgccataca tataaacacg      300
cgacgaccga tattaaggaa tgcagccaca agcttcagta agtgatggag cacttgccgg      360
atttgttcct tgcagacaag gcttcaacat tgtcgtaaaa taggagtagt aaaggtatgg      420
acagtagcag gctgcgggcc gctgtgaacc ttatctcgaa agctgggata aagcattaaa      480
gtccatcact ccaagagtgt aatcaccatg acaatctcta ttgggtcgcc aacaaggact      540
gtcgggttca gacagtgaga caagcagcag caatggccac catcgcagcc cgctcaacca      600
gctctgccgt ctcctgcggc cgcccttgca cgcagctgcg tgcaggtgcg cgctgccctg      660
```

-continued

```
aagcccagcg tgaaggccgc tcccgcggtc tccaccgctg gcgccaacca gatgatggtc    720
tggcagccca ttaacaacaa gtgcggaccc ttatccactt cctgaaaccg agctcgaccc    780
cagcctgcga cccgtcgtaa cacggcattc actgcctctt cctcgcaggc aatacgagac    840
tttctcttac ttgcctccct tgacatccga ccagattgct cgccaggtcg actatgtcgt    900
tggcaacggt tggattccat gcctggagtt cgctgacgcc agccaggcct atgtcagcaa    960
cgccagcaca gtgcgctttg ctccgtgtc cgctgtgagt gtcttaggag acatgcgtac    1020
cctatgcctt tctcgcccgt cgcctgctgc tcatgattcc agtcgattg ctctccggac    1080 tgacttttat cgtgtttgac ttttgcccga tcgcagtgct actacgacaa caggtactgg    1140
acactgtgga agctgcccat gttcggttgc actgaccct cgccgtgct gactgagatc    1200 agccgcgcct ccaaggcctt cccccaggcc tacattcgca tggtgtgtag gaacagtgtt    1260
cgcagcagca ttgtgtaaag cagcgtccgc tgttctgcag                         1300
```

<210> SEQ ID NO 8
<211> LENGTH: 31
<212> TYPE: DNA
<213> ORGANISM: Artificial sequence
<220> FEATURE:
<223> OTHER INFORMATION: Oligonucleotide probe

<400> SEQUENCE: 8

```
ccaagcagaa gtaccgcgcc tccatggagg g                                   31
```

<210> SEQ ID NO 9
<211> LENGTH: 31
<212> TYPE: DNA
<213> ORGANISM: Artificial sequence
<220> FEATURE:
<223> OTHER INFORMATION: Oligonucleotide probe

<400> SEQUENCE: 9

```
ccctccatgg aggcgcggta cttctgcttg g                                   31
```

<210> SEQ ID NO 10
<211> LENGTH: 474
<212> TYPE: PRT
<213> ORGANISM: Synechococcus elongatus
<220> FEATURE:
<223> OTHER INFORMATION: Phytoene desaterase

<400> SEQUENCE: 10

```
Met Arg Val Ala Ile Ala Gly Ala Gly Leu Ala Gly Leu Ser Cys Ala
1               5                   10                  15

Lys Tyr Leu Ala Asp Ala Gly His Thr Pro Ile Val Tyr Glu Arg Arg
            20                  25                  30

Asp Val Leu Gly Gly Lys Val Ala Ala Trp Lys Asp Glu Asp Gly Asp
        35                  40                  45

Trp Tyr Glu Thr Gly Leu His Ile Phe Phe Gly Ala Tyr Pro Asn Met
    50                  55                  60

Leu Gln Leu Phe Lys Glu Leu Asn Ile Glu Asp Arg Leu Gln Trp Lys
65                  70                  75                  80

Ser His Ser Met Ile Phe Asn Gln Pro Thr Lys Pro Gly Thr Tyr Ser
                85                  90                  95

Arg Phe Asp Phe Pro Asp Ile Pro Ala Pro Ile Asn Gly Val Ala Ala
            100                 105                 110

Ile Leu Ser Asn Asn Asp Met Leu Thr Trp Glu Glu Lys Ile Lys Phe
        115                 120                 125
```

```
Gly Leu Gly Leu Leu Pro Ala Met Ile Arg Gly Gln Ser Tyr Val Glu
    130                 135                 140
Glu Met Asp Gln Tyr Ser Trp Thr Glu Trp Leu Arg Lys Gln Asn Ile
145                 150                 155                 160
Pro Glu Arg Val Asn Asp Glu Val Phe Ile Ala Met Ala Lys Ala Leu
                165                 170                 175
Asn Phe Ile Asp Pro Asp Glu Ile Ser Ala Thr Val Val Leu Thr Ala
            180                 185                 190
Leu Asn Arg Phe Leu Gln Glu Lys Lys Gly Ser Met Met Ala Phe Leu
        195                 200                 205
Asp Gly Ala Pro Pro Glu Arg Leu Cys Gln Pro Ile Val Glu His Val
    210                 215                 220
Gln Ala Arg Gly Gly Asp Val Leu Leu Asn Ala Pro Leu Lys Glu Phe
225                 230                 235                 240
Val Leu Asn Asp Asp Ser Ser Val Gln Ala Phe Arg Ile Ala Gly Ile
                245                 250                 255
Lys Gly Gln Glu Glu Gln Leu Ile Glu Ala Asp Ala Tyr Val Ser Ala
            260                 265                 270
Leu Pro Val Asp Pro Leu Lys Leu Leu Leu Pro Asp Ala Trp Lys Ala
        275                 280                 285
Met Pro Tyr Phe Gln Gln Leu Asp Gly Leu Gln Gly Val Pro Val Ile
    290                 295                 300
Asn Ile His Leu Trp Phe Asp Arg Lys Leu Thr Asp Ile Asp His Leu
305                 310                 315                 320
Leu Phe Ser Arg Ser Pro Leu Leu Ser Val Tyr Ala Asp Met Ser Asn
                325                 330                 335
Thr Cys Arg Glu Tyr Glu Asp Pro Asp Arg Ser Met Leu Glu Leu Val
            340                 345                 350
Phe Ala Pro Ala Lys Asp Trp Ile Gly Arg Ser Asp Glu Asp Ile Leu
        355                 360                 365
Ala Ala Thr Met Ala Glu Ile Glu Lys Leu Phe Pro Gln His Phe Ser
    370                 375                 380
Gly Glu Asn Pro Ala Arg Leu Arg Lys Tyr Lys Ile Val Lys Thr Pro
385                 390                 395                 400
Leu Ser Val Tyr Lys Ala Thr Pro Gly Arg Gln Gln Tyr Arg Pro Asp
                405                 410                 415
Gln Ala Ser Pro Ile Ala Asn Phe Phe Leu Thr Gly Asp Tyr Thr Met
            420                 425                 430
Gln Arg Tyr Leu Ala Ser Met Glu Gly Ala Val Leu Ser Gly Lys Leu
        435                 440                 445
Thr Ala Gln Ala Ile Ile Ala Arg Gln Asp Glu Leu Gln Arg Arg Ser
    450                 455                 460
Ser Gly Arg Pro Leu Ala Ala Ser Gln Ala
465                 470
```